(12) United States Patent
De Luca et al.

(10) Patent No.: US 8,048,645 B2
(45) Date of Patent: Nov. 1, 2011

(54) METHOD OF PRODUCING FUNCTIONAL PROTEIN DOMAINS

(75) Inventors: Giampiero De Luca, Conches (CH); Luca Falciola, Geneva (CH)

(73) Assignee: Merck Serono SA, Coinsins, Vaud (CH)

( * ) Notice: Subject to any disclaimer, the term of this patent is extended or adjusted under 35 U.S.C. 154(b) by 0 days.

(21) Appl. No.: 10/343,684

(22) PCT Filed: Aug. 1, 2001

(86) PCT No.: PCT/GB01/03455
§ 371 (c)(1),
(2), (4) Date: Jun. 17, 2003

(87) PCT Pub. No.: WO02/10372
PCT Pub. Date: Feb. 7, 2002

(65) Prior Publication Data
US 2004/0053362 A1     Mar. 18, 2004

(30) Foreign Application Priority Data
Aug. 1, 2000   (GB) .................................... 0018876.3

(51) Int. Cl.
*C12N 15/00* (2006.01)
*C12N 15/11* (2006.01)

(52) U.S. Cl. ...................................... 435/69.1; 536/23.1

(58) Field of Classification Search ................ 435/69.1
See application file for complete search history.

(56) References Cited

U.S. PATENT DOCUMENTS

| | | | |
|---|---|---|---|
| 5,272,071 A | 12/1993 | Chappel | |
| 5,545,817 A * | 8/1996 | McBride et al. | 800/287 |
| 5,578,461 A * | 11/1996 | Sherwin et al. | 435/69.1 |
| 5,641,670 A * | 6/1997 | Treco et al. | 435/325 |
| 5,733,761 A | 3/1998 | Treco et al. | |
| 5,789,215 A * | 8/1998 | Berns et al. | 800/25 |
| 5,968,502 A | 10/1999 | Treco et al. | |
| 5,981,214 A | 11/1999 | Skoultchi | |
| 6,528,314 B1 | 3/2003 | Le Mouellic et al. | |
| 6,537,542 B1 * | 3/2003 | Treco et al. | 424/93.21 |
| 7,063,960 B2 * | 6/2006 | Choi et al. | 435/69.1 |

FOREIGN PATENT DOCUMENTS

| | | |
|---|---|---|
| WO | WO 90/11354 A1 | 10/1990 |
| WO | WO 91/06666 A1 | 5/1991 |
| WO | WO 91/09955 A1 | 7/1991 |
| WO | WO 94/12650 A2 | 6/1994 |
| WO | WO 95/31560 A1 | 11/1995 |
| WO | WO96/29411 * | 9/1996 |
| WO | WO 96/29411 A1 | 9/1996 |
| WO | WO 97/23244 A1 | 7/1997 |
| WO | WO 99/15650 A1 | 4/1999 |
| WO | WO 99/50426 A1 | 10/1999 |
| WO | WO 99/61604 A2 | 12/1999 |
| WO | WO 00/31236 A2 | 6/2000 |

OTHER PUBLICATIONS

Kulkarni, R. et al. Cell 96: 329-339 (1999).*
Kiessling, Laura L. et al.; "Transforming the cell surface through proteolysis"; *Chemistry and Biology*; Mar. 1998; 5, R49-R62.
Makrides, Savvas C.; "Componenets of Vectors for Gene Transfer and Expression in Mammalian Cells"; *Protein Expression and Purification*; 1999, 17, 183-202.
Muller, Ulrike et al.; "Ten years of gene targeting: targeted mouse mutants, from vector design to phenotype analysis"; *Mechanism of Development*;1999, 82; 3-21.
Patthy, László; "Genome evolution and the evolution of exon-shuffling—a review"; *Gene: An International Journal on Genes and Genomics*;1999; 238, 103-114.
Salminen, Marjo et al.: "Efficient Poly A Trap Approach Allows the Capture of Genes Specifically Active in Differentiated Embryonic Stem Cells and in Mouse Embryos"; *Developmental Dynamics*; 1998; 212, 326-333.
Yamaguchi, Noriko et al.; "Endostatin inhibits VEGF-induced endothelial cell migration and tumor growth independently of zinc binding"; *The EMBO Journal*; 1999; 18, 16, 4414-4423.
Yihai Cao, Endogenous angiogenesis inhibitors and their therapeutic implications, the International Journal of Biochemistry & cell Biology, 33:357-367 (2001).
Mantovani et al., Decoy receptors: a strategy to regulate inflammatory cytokines and chemokines, Trends in Immunology, 22(8):328-336 (2001).

* cited by examiner

*Primary Examiner* — Anand Desai
(74) *Attorney, Agent, or Firm* — Browdy and Neimark, PLLC

(57) ABSTRACT

The present invention provides a method of producing functional protein domains, which are fragments of primary translational products consisting of one or more distinct protein domains encoded by specific subsets of exonic sequences. The method is based on the integration, by a single homologous recombination event, of a regulatory unit into the eukaryotic gene coding for the primary translational product at the level of the intronic genomic region immediately adjacent to the exonic sequences which code for the functional protein domain.

10 Claims, 19 Drawing Sheets

FIGURE 1
A)
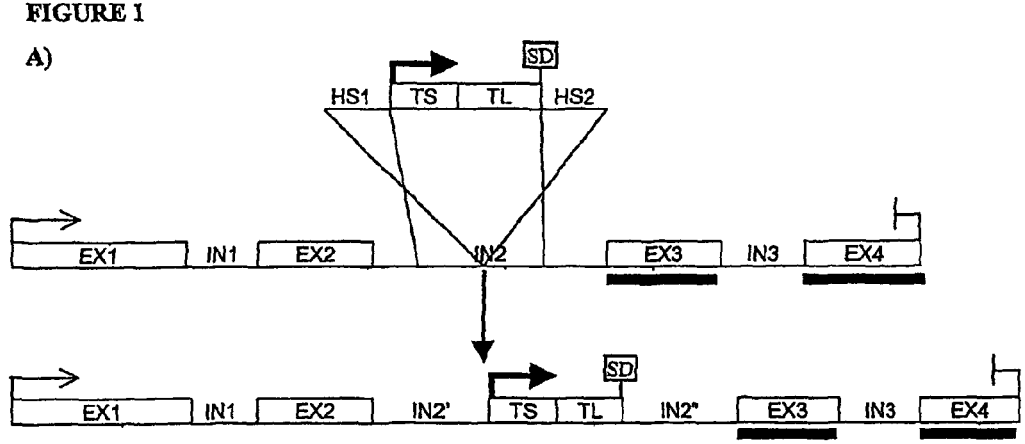
B)
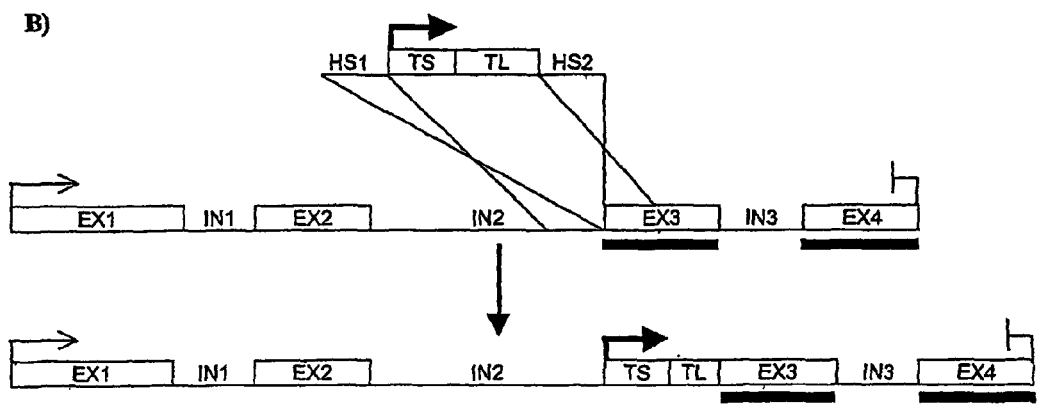
C)
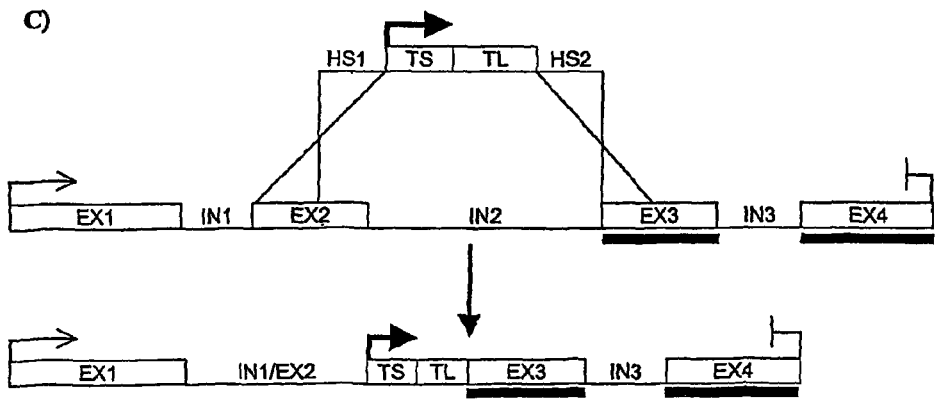

FIGURE 1
D)
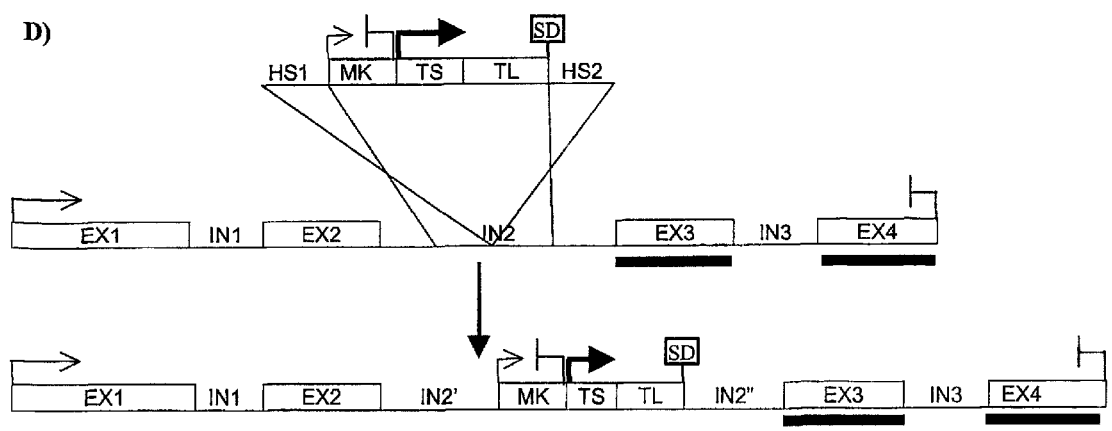
E)
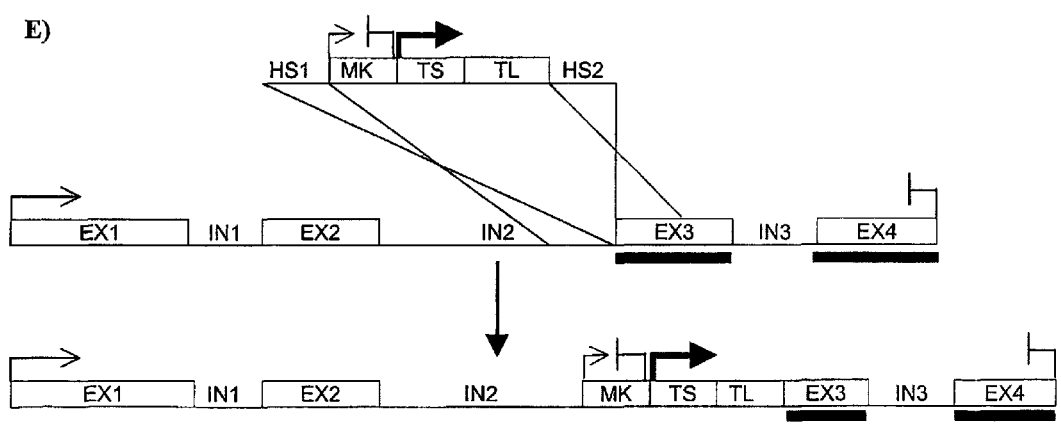
F)
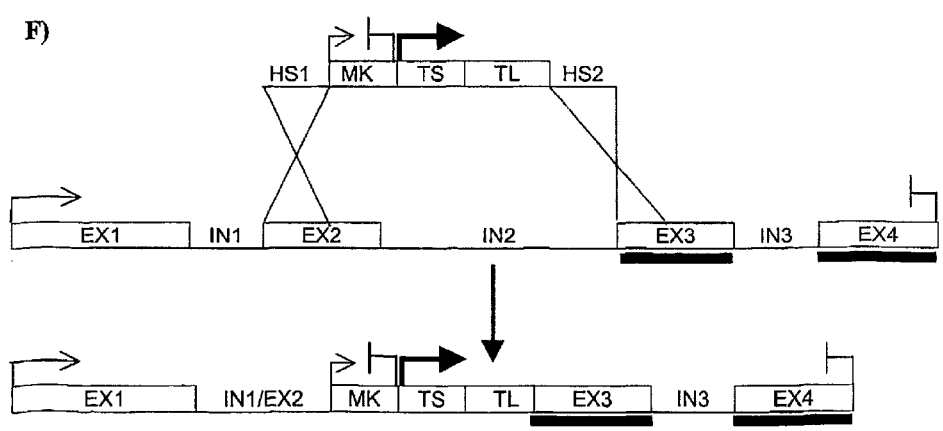

FIGURE 1
G)
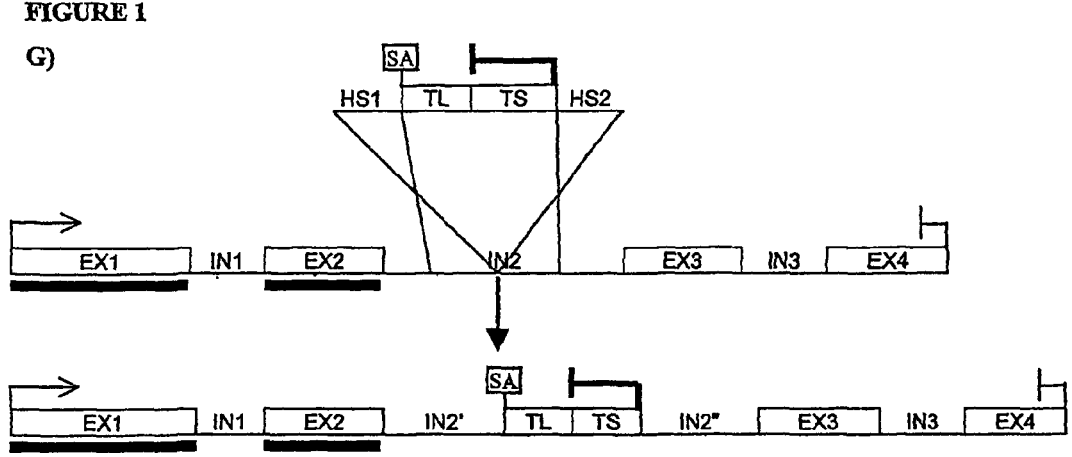
H)
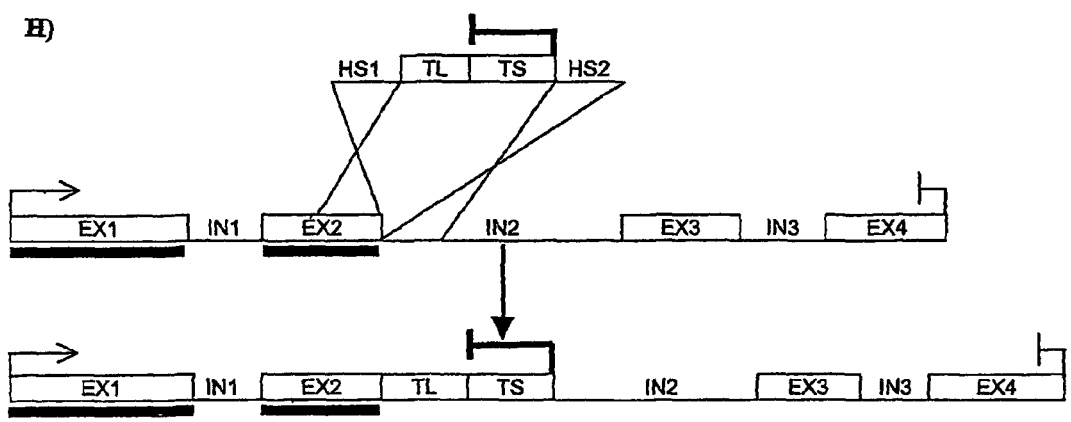
I)
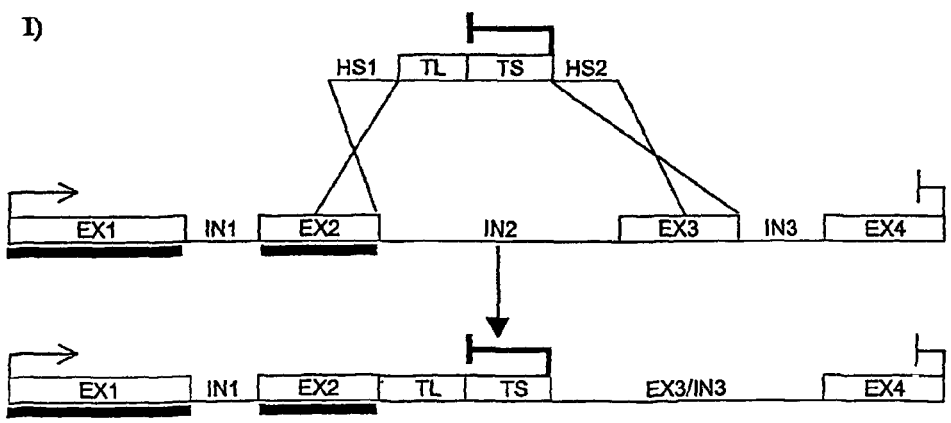

FIGURE 4
A)
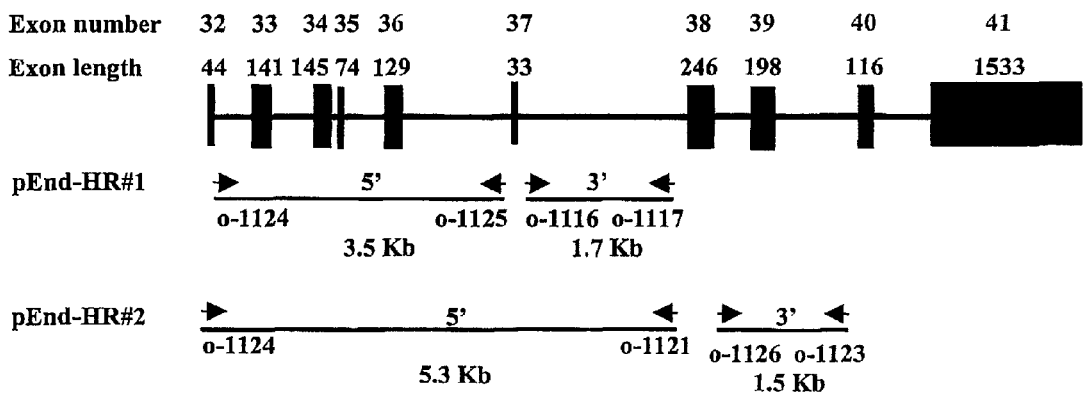
B)
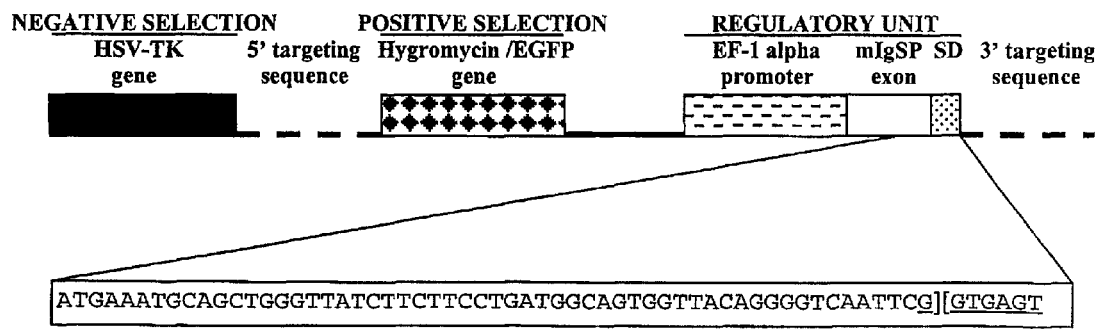

FIGURE 8

```
  1       GCACCGGACTCAGATTCGCTAGAGCGTCACCCCTAGAGTCGAGCTGTGAC
                              mIgSP exon
  1                  M  K  C  S  W  V  I  F  F  L  M  A  V
 51       GGTCCTTACAATGAAATGCAGCTGGGTTATCTTCTTCCTGATGGCAGTGG
                              mIgSP exon
 14        V  T  G  V  N  S  D  N  E  V  A  A  L  Q  P  P  V
101       TTACAGGGGTGAATTCGGACAATGAAGTGGCCGCCTTGCAGCCCCCCGTG
              mIgSP exon              exon 38
 31        V  Q  L  H  D  S  N  P  Y  P  R  R  E  H  P  H  P
151       GTGCAGCTGCACGACAGCAACCCCTACCCGCGGCGGGAGCACCCCCACCC
                                exon 38
 48        T  A  R  P  W  R  A  D  D  I  L  A  S  P  P  R
201       CACCGCGCGGCCCTGGCGGGCAGATGACATCCTGGCCAGCCCCCCTCGCC
                                exon 38
 64        L  P  E  P  Q  P  Y  P  G  A  P  H  H  S  S  Y  V
251       TGCCCGAGCCCCAGCCCTACCCCGGAGCCCCGCACCACAGCTCCTACGTG
                                exon 38
 81        H  L  R  P  A  R  P  T  S  P  P  A  H  S  H  R  D
301       CACCTGCGGCCGGCGCGACCCACAAGCCCACCCGCCCACAGCCACCGCGA
                                exon 38
 98        F  Q  P  V  L  H  L  V  A  L  N  S  P  L  S  G
351       CTTCCAGCCGGTGCTCCACCTGGTTGCGCTCAACAGCCCCCTGTCAGGCG
              exon 38                    exon 39
114        G  M  R  G  I  R  G  A  D  F  Q  C  F  Q  Q  A  R
401       GCATGCGGGGCATCCGCGGGGCCGACTTCCAGTGCTTCCAGCAGGCGCGG
                                exon 39
131        A  V  G  L  A  G  T  F  R  A  F  L  S  S  R  L  Q
451       GCCGTGGGGCTGGCGGGCACCTTCCGCGCCTTCCTGTCCTCGCGCCTGCA
                                exon 39
148        D  L  Y  S  I  V  R  R  A  D  R  A  A  V  P  I
501       GGACCTGTACAGCATCGTGCGCCGTGCCGACCGCGCAGCCGTGCCCATCG
                                exon 39
164        V  N  L  K  D  E  L  L  F  P  S  W  E  A  L  F  S
551       TCAACCTCAAGGACGAGCTGCTGTTTCCCAGCTGGGAGGCTCTGTTCTCA
              exon 39              exon 40
181        G  S  E  G  P  L  K  P  G  A  R  I  F  S  F  D  G
601       GGCTCTGAGGGTCCGCTGAAGCCCGGGGCACGCATCTTCTCCTTTGACGG
                                exon 40
198        K  D  V  L  R  H  P  T  W  P  Q  K  S  V  W  H
651       CAAGGACGTCCTGAGGCACCCCACCTGGCCCCAGAAGAGCGTGTGGCATG
                   exon 40                    exon 41
214        G  S  D  P  N  G  R  R  L  T  E  S  Y  C  E  T  W
701       GCTCGGACCCCAACGGGCGCAGGCTGACCGAGAGCTACTGTGAGACGTGG
                                exon 41
```

FIGURE 8 (cont.)

```
231       R   T   E   A   P   S   A   T   G   Q   A   S   S   L   L   G   G
751       CGGACGGAGGCTCCCTCGGCCACGGGCCAGGCCTCCTCGCTGCTGGGGGG
                                    exon 41

248       R   L   L   G   Q   S   A   A   S   C   H   H   A   Y   I   V
801       CAGGCTCCTGGGGCAGAGTGCCGCGAGCTGCCATCACGCCTACATCGTGC
                                    exon 41

264       L   C   I   E   N   S   F   M   T   A   S   K stop
851       TCTGCATTGAGAACAGCTTCATGACTGCCTCCAAGTAGCCACCGCCTGGA
                                    exon 41
```

FIGURE 9

```
1       GCACCGGACTCAGATTCGCTAGAGCGTCACCCCTAGAGTCGAGCTGTGAC
                    ◄─────────────────────────────────
                              mIgSP exon 1               M  K  C  S  W  V  I  F  F  L  M  A  V
51      GGTCCTTACAATGAAATGCAGCTGGGTTATCTTCTTCCTGATGGCAGTGG
        ──────────────────────────────────────────────────
                              mIgSP exon 14      V  T  G  V  N  S  L  H  L  V  A  L  N  S  P  L  S
101     TTACAGGGGTGAATTCGCTCCACCTGGTTGCGCTCAACAGCCCCCTGTCA
                        ──►◄──────────────────
             mIgSP exon              exon 39

31      G  G  M  R  G  I  R  G  A  D  F  Q  C  F  Q  Q  A
151     GGCGGCATGCGGGGCATCCGCGGGGCCGACTTCCAGTGCTTCCAGCAGGC
                              exon 39

48      R  A  V  G  L  A  G  T  F  R  A  F  L  S  S  R
201     GCGGGCCGTGGGGCTGGCGGGCACCTTCCGCGCCTTCCTGTCCTCGCGCC
                              exon 39

64      L  Q  D  L  Y  S  I  V  R  R  A  D  R  A  A  V  P
251     TGCAGGACCTGTACAGCATCGTGCGCCGTGCCGACCGCGCAGCCGTGCCC
                              exon 39

81      I  V  N  L  K  D  E  L  L  F  P  S  W  E  A  L  F
301     ATCGTCAACCTCAAGGACGAGCTGCTGTTTCCCAGCTGGGAGGCTCTGTT
                        ──►◄──────────────────
                exon 39              exon 40

98      S  G  S  E  G  P  L  K  P  G  A  R  I  F  S  F
351     CTCAGGCTCTGAGGGTCCGCTGAAGCCCGGGGCACGCATCTTCTCCTTTG
                              exon 40

114     D  G  K  D  V  L  R  H  P  T  W  P  Q  K  S  V  W
401     ACGGCAAGGACGTCCTGAGGCACCCCACCTGGCCCCAGAAGAGCGTGTGG
                                      ──►◄──────────────
                              exon 40              exon 41

131     H  G  S  D  P  N  G  R  R  L  T  E  S  Y  C  E  T
451     CATGGCTCGGACCCCAACGGGCGCAGGCTGACCGAGAGCTACTGTGAGAC
                              exon 41

148     W  R  T  E  A  P  S  A  T  G  Q  A  S  S  L  L
501     GTGGCGGACGGAGGCTCCCTCGGCCACGGGCCAGGCCTCCTCGCTGCTGG
                              exon 41

164     G  G  R  L  L  G  Q  S  A  A  S  C  H  H  A  Y  I
551     GGGGCAGGCTCCTGGGGCAGAGTGCCGCGAGCTGCCATCACGCCTACATC
                              exon 41

181     V  L  C  I  E  N  S  F  M  T  A  S  K  stop
601     GTGCTCTGCATTGAGAACAGCTTCATGACTGCCTCCAAGTAGCCACCGCC
                              exon 41
```

FIGURE 10
A)
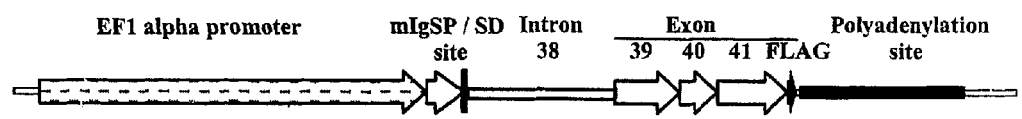
B)
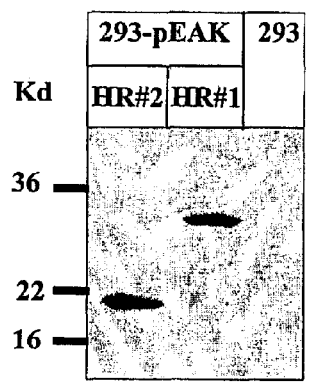
C)
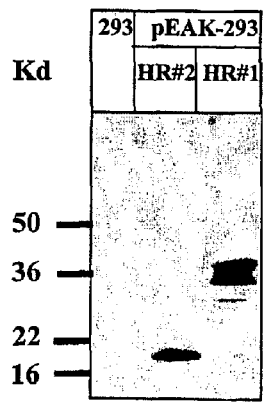

FIGURE 11
A)
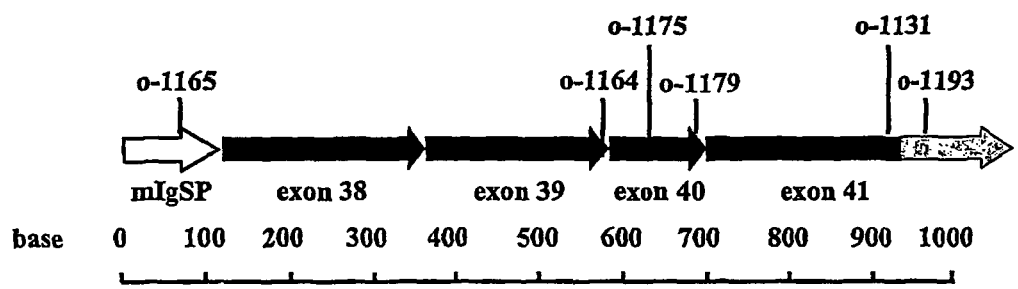
B)
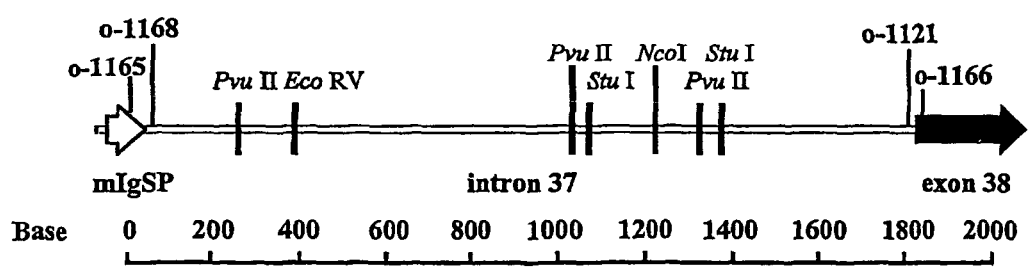

A = o-1164
B = o-1175
C = o-1179
D = o-1131

FIGURE 14
A)
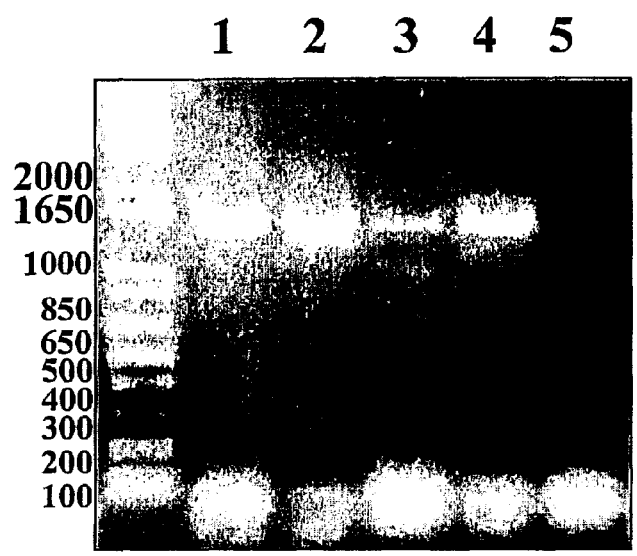
B)
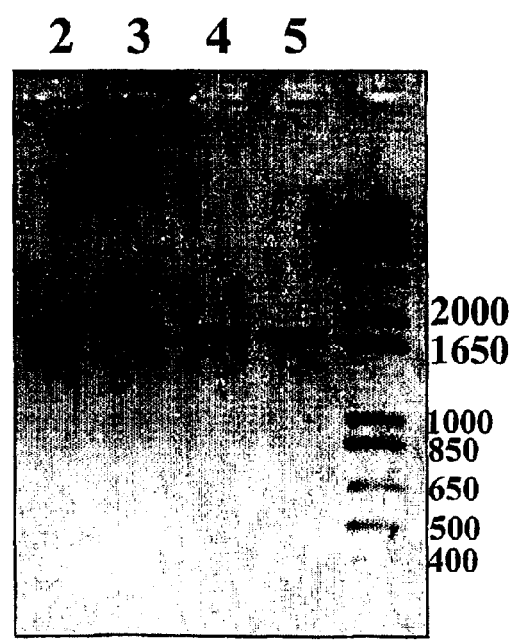

A)

B)

|          | (1)                  | (2)                  |
|----------|----------------------|----------------------|
| Uncut    | 1784                 | 1821                 |
| Eco RV   | 1418, 366            | 1427, 394            |
| Nco I    | 1192, 592            | 1220, 601            |
| Stu I    | 1052, 425, 307       | 1080, 434, 307       |
| Pvu II   | 781, 497, 294, 212   | 781, 506, 294, 240   |

METHOD OF PRODUCING FUNCTIONAL PROTEIN DOMAINS

This invention relates to a method for the production of proteins, in particular of functional protein domains.

BACKGROUND OF THE INVENTION

The functionality of a protein is tightly connected with its structural properties, which are organized into different levels: the primary structure (corresponding to the amino acid sequence encoded by the gene), the secondary structure (preferred relative backbone locations of sequentially consecutive residues), tertiary structure (the relative position of all atoms of a polypeptide chain), and quaternary structure (the arrangement of different protein subunits, each corresponding to a distinct polypeptide chain, into a complex).

In addition to these levels of organization, a polypeptide of interest may correspond to a protein domain, which can be defined in two ways. From a structural perspective, a domain is a region of compactly folded polypeptide comprising one or more secondary and/or tertiary structures. Small proteins (<100 amino acids) are often composed of a single structural protein domain, while larger proteins usually consist of multiple structural protein domains. In the three-dimensional structure of a protein, a structural protein domain is seen as a unit of independently folded polypeptide that is well distinct from other parts of the protein. Associated with this structural definition, a second view of a protein domain is that it is the smallest piece of a protein that retains a function, resulting from its interaction with one or more proteins, nucleic acids, sugars, lipids, or any other organic or inorganic compound. A functional domain is generally composed of 50-350 amino acids and therefore may consist of one or more structural domains.

In nature, proteins can contain one or more functional protein domains, sequentially linked to each other and arranged tridimensionally. While the assignment of a particular amino acid sequence to a class of structural domains is possible by NMR or X-ray crystallography, the demonstration that a protein sequence is associated to a function is mostly obtained by identifying sequence homologies to known functional protein domains and/or by generating altered forms of the original protein to be tested in a relevant biochemical or biological assay in the so-called structure-activity or structure-function studies.

Many proteins share highly homologous functional and/or structural protein domains, probably as a consequence of a process called "exon shuffling". According to this evolutionary theory, a certain number of genes have been created through a series of duplications, intronic recombinations, combinatorial assembly and mutations of existing exons coding for protein "modules" (Patthy L, Gene (1999), 238(1): 103-114).

The idea that protein evolution in eukaryotes is also mediated by sexual intronic homologous recombination of parental genomes, creating new genes from the combination of exons associated to specific protein domains, is now widely accepted also because a series of studies demonstrate a relationship between the phase and the position of introns to the structural boundaries between protein domains (de Souza S J et al., Proc Natl Acad Sci USA. (1996), 93(25): 14632-6). In a significant number of situations it is evident that protein modules are associated to one or more exons limited by introns having phase zero (the intron does not interrupt a codon) or having always the same phase. In this way the exons coding for such "mobile" domains can be more easily combined into novel proteins composed by mosaic of such protein modules, without any problem of frame (de Souza S J et al., Proc Natl Acad Sci U S A. (1998), 95(9): 5094-9; Kolkman J A and Stemmer W P, Nat Biotechnol. (2001), 19(5): 423-8).

However, it has been also shown that a functional protein domain can exert biological activities clearly distinct from the one exerted in the context of the complete protein when it is physically separated from the rest of the primary translational product, that is, the protein obtained by directly translating the mRNA transcribed from a gene. Such functional protein domains are obtained in vivo following a proteolytic cleavage, which can be executed by an endopeptidase produced either by the cell encoding the primary translational product itself or by other cells, for example, when the primary translational product is secreted or exposed onto the cellular membrane. Such events are becoming more and more frequently characterized and it is evident that the functional protein domains so produced may have important physiological activities (Kiessling L L and Gordon E J, Chem. Biol. (1998), 5(3): R49-R62; Halim N S, The Scientist (2000), 1 (16): 20; Blobel C P, Curr. Opin. Cell Biol. (2000), 12(5): 606-612).

A number of commercially valuable Eukaryotic proteins correspond to these functional protein domains which, in a certain number of cases, are encoded by a subset of the coding exons making up the full gene.

An example is endostatin, an endogenous inhibitor of angiogenesis and tumor growth, which corresponds to the C-terminal proteolytic fragment of Collagen XVIII 1alpha, a collagenous protein of the extracellular matrix. Endostatin is encoded essentially by the 3 exons at the 3' end of the Collagen XVIII 1alpha (COL18A1) gene but it is fully functional only after being released by proteolysis from Collagen XVII-I.alpha-1, the primary translational product (O'Reilly M S et al., Cell (1997), 88(2): 277-285).

Another example is Tumor Necrosis Factor (TNF)-related activation-induced cytokine (also called TRANCE, RANKL, OPGL, or ODF), a type II transmembrane protein that is involved in the signaling pathway activating the rapid induction of genes that trigger osteoclast development. TRANCE is made as a membrane-anchored primary translational product, which is cleaved by the metalloprotease-disintegrin TNF-alpha convertase (TACE), generating a soluble TRANCE, a fully functional protein having potent dendritic cell survival and osteoclastogenic activity. The sequence of this soluble protein corresponds to the one encoded by the last 3 exons of the TRANCE gene (Lum L et al., J. Biol. Chem. (1999), 274(19): 13613-8).

For the commercial-scale production of a functional protein domain, there are two main alternatives, each having its drawbacks.

One could attempt to emulate nature, and produce in the first instance the primary translational product, which is subsequently proteolytically processed to obtain the desired protein.

To conduct this whole process by recombinant DNA technology is technically demanding. Not only the primary translational product has to be expressed, but also the proteolytic enzyme specific for the desired functional protein domain has to be identified, expressed and allowed to interact with the primary translational product, either in a cellular model or in an in vitro system, to ensure appropriate cleavage before further processing.

As a second approach, an expression construct, containing only the DNA coding sequence for the functional protein domain isolated from the original mRNA or gene, can be prepared. Even this commonly used technology requires a series of operations which may sensibly delay the development of a recombinant product (Makrides S C, Protein Expr. Purif (1999), 17(2): 183-202; Kaufman R J, Mol. Biotechnol. (2001), 16(2): 151-60). It is necessary to isolate the coding sequence of interest from the full cDNA sequence, which has to be modified so that it can be further subcloned into an expression vector containing all the transcription and translation control elements necessary for the correct expression in the host cell. The construct is then used to transform the host cell and, finally, a screening procedure is applied to the transformants to isolate clones expressing the exogenous protein, correctly and at high level.

The isolation of relevant clones can be time-consuming since ordinary expression vectors, in addition to the requirements listed previously, need to recombine with the genomic sequence of the host cell. Expression constructs maintained extrachromosomally are unstable and allow only a transient expression of the protein, usually insufficient to allow production on a commercial scale.

Therefore, a recombination event involving coding and non-coding exogenous DNA and host cell genomic DNA is necessary to transmit the expression construct to all cells generated by the subsequent cycles of DNA replication and mitotic division of the originally transformed cell. This process is also completely random and error-prone, since no specific features of the expression vector can drive the complete incorporation of the exogenous sequence into the host cell genome. Thus, any part of it, having even a very low homology with any endogenous sequence, can be used by the cell for non-homologous recombination events, which are known to be orders of magnitude more frequent than homologous recombination, often resulting in the incomplete integration of the necessary exogenous sequences.

These problems lead to the development of genetic enrichment and selection procedures whose purpose is to eliminate transformants where the expression construct has been integrated in an incomplete form. Since some essential parts of the exogenous sequence may have been lost or altered during the recombination process, the coding sequence of interest may be mutated, truncated, or not expressed at all. In any case, a vast majority of transformants, whatever technique is used to introduce the DNA and select the cells, fail to produce the expected protein.

Finally, it is well established in the literature that the correct expression of recombinant proteins in eukaryotic cells depends on many factors related to the specific host cell. Features like the toxicity of the recombinant protein, mRNA processing and stability, and other post-translational events are strictly related to the product itself, to both coding and non-coding sequence in the expression vector, and to the interaction of exogenous sequences with the genomic background of the host cells. In fact, the random insertion of a complete recombinant gene, which may contain many Kilobases of DNA, may severely perturb the genome of the host cell, compromising its stability and viability. Therefore, even if the exogenous sequences have been entirely integrated, some clones cannot be used to produce the protein whenever such sequences disrupt genomic sequences important for cell metabolism and/or replication. Such clones may be lost due to selective pressure in the cell culture, or they replicate so slowly that it is difficult to obtain enough cells stably expressing the desired protein with a satisfying efficiency.

Alternative strategies have been developed in order to minimize the drawbacks of essentially uncontrolled exogenous gene integration. They are mostly based on homologous recombination, a unique technology allowing insertion of a specific exogenous sequence into a predetermined genomic sequence of a mammalian cell. This technique has been mostly used for the characterization of genes or regulatory sequence in animal and cell models by modifying them, as recently reviewed (Muller U, Mech. Dev. (1999), 82(1-2): 3-21; Sedivy J M and Dutriaux A, Trends Genet. (1999), 15(3): 88-90), generating disrupted, non-functional or chimeric genes. Various vectors and selectable marker genes have been introduced, for example, in the genome of mouse Embryonic Stem (ES) cells, in order to study the effects of genetic alterations on various phenotypic features, like hormonal regulation, fertility, immunological response, organ development.

The feasibility of homologous recombination-based techniques for the production of recombinant proteins has been demonstrated at the level of entire primary translational products (WO 91/09955, WO 95/31560), which have been obtained by putting a complete endogenous gene under the control of exogenous transcriptional regulatory sequences. Alternatively, truncated proteins may be obtained by antisense oligonucleotides that, once transfected into a cell, can pair to the endogenous mRNA blocking the ribosome to go through the entire coding sequence (WO 97/23244). However, none of the documents in the literature suggests the use of homologous recombination for expressing selectively one or more exons of an endogenous target gene encoding a functional protein domain comprised in a primary translational product by integrating exogenous regulatory sequences.

SUMMARY OF THE INVENTION

It has now been found that, when the functional protein domain corresponds to the N- or C-terminus of a primary translational product, for example encoded by at least the 5'- or 3'-, respectively, most exon(s) of an intron-containing gene, there is a further method by which the functional protein domain may be produced.

Thus, according to a first aspect of the invention, there is provided a method of producing a protein, which is a functional protein domain that corresponds to the C- or N-terminus of a primary translational product of a gene, wherein the protein has a biological activity which is distinct from that of the primary translational product the method comprising:

(i) growing a host cell transfected with a DNA construct comprising:
(a) a regulatory DNA sequence capable of either initiating transcription and translation or terminating transcription and translation of the DNA encoding the protein; and
(b) a DNA targeting region comprising sequences homologous to a genomic region 5' or 3', respectively, to the sequence coding for the protein, the construct being integrated within the host cell genomic DNA at a position determined by the DNA targeting segment such that expression of the protein is under the control of the regulatory DNA;
(ii) culturing the homologously recombinant cell; and
(iii) collecting the functional protein domain.

The invention is useful for producing proteins, which form functional protein domains in cells wherein the one or more coding exons lack, at one end, the regulatory DNA sequence necessary for their expression and direct translation as distinct molecular entities, and not as segments of primary translational products. Included within the term proteins are included short peptides and oligopeptides (containing for example up to thirty amino acid residues) as well as longer polypeptides (containing over thirty amino acid residues). Peptides and polypeptides producible by means of the invention include those which are produced by proteolytic maturation of a primary translational product.

The present invention discloses also a method for selectively expressing the exon(s) encoding for a functional protein domain whose sequence corresponds to either the C- or N-terminal sequence of a primary translational product of a gene, wherein the protein encoded by said exon(s) has a biological activity which is distinct from that of the primary translational product, the method comprising growing a host cell transfected with a DNA construct comprising:
(a) a regulatory DNA sequence capable of either initiating transcription and translation or terminating transcription and translation of the exon(s) encoding the protein corresponding to the functional protein domain; and
(b) a DNA targeting region comprising sequences homologous to a genomic region 5' or 3', respectively, to the exon(s) coding for the protein, the construct being integrated within the host cell genomic DNA at a position determined by the DNA targeting segment such that expression of the exon(s) is under the control of the regulatory DNA.

The host cell modified with the method of the invention selectively expresses the exonic sequences present in the genome coding for a functional protein domain as a novel mRNA molecule which is directly translated into the functional protein domain, without any specific cell- or tissue-type proteolytic modification.

In preferred embodiments, the peptide or polypeptide forming the functional protein domain is coded by at least the 5'- or 3'-most exon of an intron containing gene. Thus, in a first preferred embodiment there is provided a method of producing a protein which is a functional protein domain that corresponds to the C-terminus of a primary translational product of a target gene and is coded by at least the 3'-most exon of an intron-containing target gene, the method comprising:
(i) growing a host cell transfected with a DNA construct which is operatively linked to said exon(s) following the integration in the host cell genome by homologous recombination, said construct comprising:
    (a) a DNA targeting region comprising sequences homologous to a genomic region 5' to the exon(s) coding for the protein;
    (b) a transcription module consisting of a DNA sequence capable of activating the transcription of a DNA encoding the functional protein domain;
    (c) a translation module consisting of a DNA sequence capable of initiating the translation of the functional protein domain; and optionally
    (d) a splicing module comprising an unpaired 5' splice donor site which, by complementing the unpaired 3' splice acceptor site of the endogenous exon encoding the N-terminus of the functional protein domain, allows the splicing of the primary transcript, resulting in the "in-frame" juxtaposition of the translation module to the sequence coding for the functional protein domain;
(ii) culturing the homologously recombinant cell; and
(iii) collecting the functional protein domain.

Suitably, in this embodiment of the invention, the construct should provide exogenous sequences forming a regulatory unit which allows the correct transcription and translation initiation for the exon(s) encoding the functional protein domain. The DNA targeting region will be formed by sequences belonging to the genomic region 5' to the sequence coding for the functional protein domain protein (such as the adjacent intron of the target gene at its 5' end), with or without sequences belonging to the exon(s) encoding the functional protein domain. If it is necessary to increase the length of the homology region, DNA sequences belonging to contiguous coding and/or non-coding sequences of the target gene (or eventually of contiguous genes) may also be included.

The Methionine (ATG) codon necessary to start the translation has to be in good Kozak sequence context, and it can be provided by the intron 5' to the exon(s) coding for the functional protein domain, by the exon containing the N-terminus of the functional protein domain, or operatively linked to endogenous coding sequences by the addition of one or more natural or synthetic exons, inserted between the exon(s) encoding for the functional protein domain, and the exogenous sequences comprised in the regulatory unit in order to initiate transcription. If the translation initiation codon is endogenous, the transcriptional module will comprise an appropriate 5' untranslated region.

The splicing module, containing an unpaired splicing donor site, is associated to the natural or synthetic exon adjacent to the exon coding for the N-terminus of the functional protein domain. The splicing module should allow the Methionine codon, once that it is put in the same frame of the functional protein domain following the splicing process, to become the N-terminal residue of the functional protein domain. In this embodiment, the target gene encoding for the primary translational product may or may not be already expressed at significant levels, but the exogenous regulatory sequence should allow to have a new transcriptional and the translational initiation site in 5' to the exon(s) coding for the functional protein domain.

Some examples of carrying out this embodiment of the invention are shown in FIG. 1A-F In a second preferred embodiment of the invention there is provided a method of producing a protein which is a functional protein domain that corresponds to the N-terminus of a primary translational product of a target gene and is coded by at least the 5'-most exon of an intron-containing target gene, the method comprising:
(i) growing a host cell transfected with a DNA construct, which is operatively linked to said exon(s) following the integration in the host cell genome by homologous recombination, said construct comprising
    (a) a DNA targeting region comprising sequences homologous to a genomic region 3' to the exon(s) coding for the protein;
    (b) a transcription module consisting of a DNA sequence capable of terminating the transcription of the genomic DNA;
    (c) a translation module consisting of a DNA sequence capable of terminating the translation of the functional protein domain; and optionally
    (d) a splicing module comprising an unpaired 3' splice acceptor site which, by complementing the unpaired 5' splicing donor site of the endogenous exon encoding the C-terminus of the functional protein domain, allows the correct splicing of the primary transcript, resulting in the "in-frame" juxtaposition of the translation module to the sequence coding for the functional protein domain;
(ii) culturing the homologously recombinant cell; and
(iii) collecting the functional protein domain.

Suitably, in this embodiment of the invention, the construct should provide exogenous sequences allowing the correct transcription and translation termination for the exon(s) encoding the protein forming the functional protein domain. The DNA targeting region will be formed by sequences belonging to the genomic region 3' to the sequence coding for the functional protein domain protein (such as the adjacent intron of the target gene at its 3' end), with or without sequences belonging to either the exon encoding the C-terminus of the protein or the intron at its 3' end, or both. If it is necessary to increase the length of the homology region, DNA sequences belonging to contiguous coding and/or non-coding sequences of the target gene (or eventually of contiguous genes) may be included.

The codon necessary for terminating translation could be either provided by the intron 3' to the exon(s) coding for the functional protein domain or operatively linked to endogenous coding sequences by the addition of natural or synthetic exon(s), inserted between the exon(s) encoding for the functional protein domain, and the exogenous sequences introduced by homologous recombination in order to terminate transcription. If the translation stop codon is endogenous, the transcriptional module will comprise an appropriate 3' untranslated region.

The splicing module, containing an unpaired splicing acceptor site, is associated to the natural or synthetic exon proximal to the exon coding for the C-terminus of the functional protein domain. The splicing module should allow the stop codon, once that it is put in same frame of the functional protein domain following the splicing process, to become the terminating codon of the functional protein domain. In this embodiment, the target gene encoding for the primary translational product has to be already expressed at significant levels and the exogenous sequence are necessary only to stop the transcription and the translation at a different position.

Some examples of carrying out this embodiment are shown in FIG. 1 G-L.

In a further aspect, the invention provides constructs which allow the host cell, once correctly integrated in the genome by homologous recombination, to express a novel mRNA including, amongst all the exons contained in the target gene encoding the primary translational product, only the one(s) encoding a functional protein domain.

The choice of the strategy for the homologous recombination affects the final structure of the target gene, since the regulatory unit can either become inserted in the adjacent intron, or replace part of this intron and the entirety or part of the genomic region belonging to the same gene but not coding for the functional protein domain.

The regulatory unit, integrated by homologous recombination in the gene comprising the exon(s) coding for a functional protein domain, contains exogenous sequences including a transcription module, a translation module, and, optionally, a splicing module. Such exogenous sequences are intended to provide the necessary sequences to be combined with the endogenous sequences encompassing the functional protein domain. Thus, a new recombinant gene should be present in the genome of the host cell, containing endogenous transcriptional and translational control elements at one end, endogenous exon(s) and intron(s) associated to the functional protein domain in the middle, and exogenous transcriptional and translational control elements at the other end.

The present invention provides a method of producing functional protein domains, which are fragments of primary translational products consisting of one or more distinct protein domains encoded by specific subsets of exonic sequences. The method is based on the integration, by a single homologous recombination event, of a regulatory unit into the eukaryotic gene coding for the primary translational product at the level of the intronic genomic region immediately adjacent to the exonic sequences which code for the functional protein domain. Depending on the position of the relevant exonic sequences in the target gene, such intron is the one immediately in 5' or 3' to the exonic sequences when the functional protein domain is, respectively, at the C- or N-terminus of the primary translational product.

The present invention provides some important advantages over the state of the art. The production of functional protein domain is achieved by the methods known in the art by isolating the coding sequence either of the functional protein domain, and expressing it under the control of regulatory sequence positioned at its extremities, or of the primary translational product and of the specific protease generating the functional protein domain, and expressing both.

The invention provides a method to produce functional protein domains whenever they are either C- or N-terminal fragments of a primary translational product and the exon/intron structure of the corresponding genomic DNA is known. This method involves the integration of exogenous regulatory sequences in 5' (if the functional protein domain corresponds to a C-terminal fragment) or 3' (if the functional protein domain corresponds to a N-terminal fragment) to the exon(s) encoding these protein domains in the genomic DNA. The methods of the invention allow to generate a recombinant gene which can be directly transcribed and translated by the cell into a functional protein domain, in contrast with the gene encoding the primary translational product.

The methods of the invention based on the properties of homologous recombination allow a controlled and precise modification of the host cell genome in order to produce a functional protein domain. The amount of exogenous sequence to be integrated in the host cell genome is very limited since, as coding sequence, the original coding sequence present in the host cell genome itself is used. Moreover, only those additional elements, such as transcription and/or translation control elements, as are necessary are actually integrated.

The use of the host cell sequence encoding the functional protein domain also provides the advantages of both eliminating any recombination-derived alteration of such coding sequence, and also making use of the same post-transcriptional (e.g. splicing) and/or post-translational (e.g. glycosylation, phosphorylation) processes that are actually applied in vivo for the maturation of the functional protein domain. The use of a single regulatory unit eliminates the necessity of manipulating the complementary DNA coding for the primary translational product to isolate the segment coding for the functional protein domain, and adapt it to the expression vector.

Finally, it has been demonstrated that genomic expression constructs (i.e. containing one or more synthetic and/or natural introns) are expressed more efficiently than identical constructs lacking introns (i.e the ones generally obtained using techniques disclosed in the literature), probably due to the splicing process. The methods of the invention avoid introducing exogenous intronic sequences by making use of introns naturally interrupting the sequence coding for the functional protein domain.

DETAILED DESCRIPTION OF THE INVENTION

In the following paragraphs, the basic elements of the invention will be appropriately described by reference to literature on homologous recombination techniques (Muller U, Mech. Dev. (1999), 82(1-2): 3-21; Hasty P et al., in "Gene targeting: a practical approach", ed. Joyner A L, pub. Oxford Univ. Press, 1999, 1-35) and protein expression techniques (Makrides S C., Protein Expr Purif. (1999), 17(2): 183-202; Kaufman R J, Mol Biotechnol. (2001), 16(2): 151-60).

The Functional Protein Domains

The expression "functional protein domain" (FPD) means a fragment of a protein being the primary translation product of a gene, which exerts a biological function. The functional protein domain, which can be composed of one or more structural protein domains (identical or different to each other), should contain all the biophysical features necessary to fold properly as an independent folded unit and exert the expected biological activity.

In the context of the genomic DNA of a cell, a functional protein domain is encoded by a portion of the entire coding region of a gene; meanwhile the primary translational product is encoded by the entirety of the coding sequence of a gene. The genomic sequence encoding a functional protein domain lacks, at either one or both extremities, appropriately positioned regulatory sequences, which are recognized by the expression machinery of the cell to generate a primary transcriptional and translational primary product. Consequently, a functional protein domain corresponds to a portion of the translated region comprised in the mRNA transcribed by a cell, and cannot result from an alternative splicing event, which would need active regulatory sequence at both ends.

Thus, a gene, having a complete and functional reading frame limited by transcription and translation regulatory sequences at the extremities, or a mRNA coding for a functional protein domain, does not exist, since there is not a genomic DNA which can be directly transcribed and translated into a protein corresponding to a functional protein domain. A cell can produce a functional protein domain, starting from a gene comprised in its own genome and in which the coding sequence for such a protein is embedded, only after the transcription and the translation of the gene into a primary translation product, which is later modified by a specific proteolytic event.

In the sense of the present invention, the proteolytic events originating a functional protein domain are not the ones simply determining the localization of a protein, like when the signal peptide is recognized and eliminated in extracellular or transmembrane proteins. Proteolytic events originating a functional protein domain have rather to be intended as the ones that allow a functional protein domain, by separating it from the primary translational product, to perform one or more biological activities providing physiological effects distinct from the ones provided by the primary translational product. Similar proteolytic activities are not expressed constitutively by any cell, like in the case of the enzyme eliminating the signal peptide, but are specifically expressed only by certain cell types or only in certain metabolic conditions.

Given that the function of a protein sequence results from its interaction with other proteins, nucleic acids, lipids, sugars, or any other organic or inorganic ligand, a functional protein domain, in sense of the present invention, is defined by relating distinctive properties with the interaction properties, identifying three basic groups.

A first group of functional protein domains is the one in which the distinctive effects are due to fact that the functional protein domain, isolated or in the context of the primary translational product, maintains the same interaction properties, in terms of ligand specificity and affinity, but, when separated from the rest of the primary translational product, it does not allow the cell or the organism to identify the presence of such ligand. Examples are provided by the extracellular binding domains of membrane receptors that, when separated proteolytically from the transmembrane and intracellular portions of the receptor by extracellular proteases, subtract the ligand to the membrane receptors and block the consequent activation of the intracellular signaling pathway.

Shed extracellular domains are functional protein domains in the sense of the present invention, since they have the effect of trapping the ligand and silencing the signaling pathway, preventing the specific cellular response, instead of signaling to the cell the presence of the ligand, as when they are linked to the rest of the primary translational product. Such functional protein domains, often named as decoy receptors, play an important physiological role, since give the possibility to the organism of finely regulating, for example, the effects of circulating chemokines and cytokines (Mantovani A et al,. Trends Immunol. (2001), 22(6): 328-36).

A second group of functional protein domains is the one in which the distinctive effects are due to fact that the functional protein domain, when isolated from the context of the primary translational product, recognizes with high affinity a ligand not or poorly bound by the primary translational product, determining an unexpected physiological effect. Examples of such fictional protein domains having important physiological effects, such as the proteolytic fragments of structural extracellular matrix proteins having strong antiangiogenic properties (Cao Y, Int. J. Biochem. Cell. Biol. (2001), 33(4): 357-69), are more and more frequently described in literature, showing that proteins may also function as reservoirs of functional protein domains which are cryptic into the primary translational product until a proteolytic event, in the frame of a specific physiological mechanism, allows them to be an isolated and functional form.

A third group of functional protein domains is represented by proteins released proteolytically from an inactive precursor protein. Many signaling and secreted proteins exert their physiological function only after being separated from the primary translational product, like proinflammatory cytokines (Dinarello C A, Chest (2000), 118 (2): 503-508).

Functional protein domains can be identified using different procedures. Traditionally functional protein domains are identified by exposing a protein to a series of proteases having different specificity and testing the activity of the resulting fragments (Carrey E., in "Protein Structure: a practical approach", ed. Creighton T., Oxford Univ. Press (1989), 117-144). This procedure offers the advantages of quickness, simplicity, and sensitivity but it is limited by the amount of complete native protein to digest, by the specificity of the proteases, and by sensitivity of the assay used to validate the proteolytic fragment as a functional protein domain.

Moreover, the advances made in the field of protein isolation and sequencing (e.g. mass spectroscopy, bidimensional gels), together with the advances in the field of bioinformatics, allow the parallel analysis of many protein samples, obtaining information on the identity and quantity of even the less represented molecular species (Lottspeich F., Angew. Chem. Int. Ed. Engl. (1999); 38(17): 2476-2492). For example, it is now possible to identify and isolate most, if not all, protein present in a mixture of proteins, unfragmented or obtained after a controlled digestion with a specific proteolytic enzyme of the whole protein content in a biological sample, even without a preliminary fractionation (Spahr C S et al., Proteomics (2001), 1(1): 93-107). By combining these technologies of protein digestion, detection, isolation, sequence comparison, and analysis to an appropriate cell biology- or biochemistry-based high throughput assay (Kuhlmann J, Int. J. Clin. Pharm. and Ther., (1997), 35 (12): 541-552), novel functional protein domains can be identified.

Important physiological activities have been found to be subjected to fine regulation by the proteolytic activity exerted by proteases such as matrix metalloproteinases (Raza S L and Cornelius L A, J. Investig. Dermatol. Symp. Proc. (2000), 5(1):.47-54) and caspases (Los M et al., Trends Immunol.

(2001), 22(1): 31-4), going far beyond the simple degradation of proteins. Moreover, since proteases should account for 1.5-2% of total gene content in humans (Southan C, J Pept Sci. (2000), 6(9): 453-8) and since protease cleavage site motifs associated to specific proteins can be more and more easily identified (Turk B E et al., Nat. Biotech. (2001), 19(7): 661-7), the variety of proteases and of proteins that can be tested will increase, and consequently the possibility to identify functional protein domains of therapeutic and commercial interest will also increase.

Once identified a functional protein as being the N- or C-terminus of a primary translational product, and found a correlation between the protein domain organization and the exon/intron organization of the corresponding gene, constructs containing the regulatory unit and the appropriate targeting regions can be used for generating cells expressing such protein species according to the methods of the invention.

The choice of the exon(s) to be expressed as a functional protein domain can be affected not only by the evidences provided by analyzing samples of fragmented or unfragmented proteins but also by the results obtained by combining the information on the calculated protein tridimensional structure, the homology with other known functional protein domains, mutagenesis and structure-function studies, or other modeling and computer simulation.

Even if the functional protein domain has not been initially in vivo or in vitro characterized as corresponding exactly to a discrete number of exons, the structure and/or the homologies of the protein sequence may be as such that the essential elements of the functional protein domain can be identified as being encoded by specific N- or C-terminal exon(s). It is not necessary for the functional protein domain produced by the methods of the invention to have N- or C-terminal residues identical to the ones initially identified ill vivo or in vitro, but to exert a comparable activity.

Further validation and characterization of a proteolytic fragment being a functional protein domain can be obtained by other method of functional screening involving molecular biology techniques like random PCR/deletion mutagenesis, mapping of the proteolytic cleavage sites, phage-display, two-hybrid system (WO 96/31625; WO 90/04788; Parry S et al., Biochem Biophys Res Commun. (2001), 283(3): 715-20; Kawasaki M, and Inagaki F, Biochem Biophys Res Commun. (2001), 280(3):842-4.), or involving non-homology based methods (Marcotte E M, Curr Opin Struct Biol. (2000), 10(3): 359-65; WO 00/11206). Before applying the methods of the invention to produce a functional domain on a large scale, fragments of different lengths belonging to a primary transcriptional product can be produced on a small scale by common expression technologies and tested in an assay to circumscribe the minimal or sufficient protein sequence corresponding to a functional protein domain.

Finally, a growing number of internet-available algorithms and software (Teichmann S A et al., Curr. Opin. Struct Biol. (2001), 11(3): 354-63; Skolnick J and Fetrow J S, Trends Biotechnol. (2000):18(1)34) can be used, separately or in combination, to compare a protein or a DNA sequence of unknown function (like the ones obtained by translating ESTs or the output of genomic sequencing programs) with databases of protein or DNA sequences with known structure and/or biological activity. This in silico procedure permits a good approximation of the position and the function of a protein domain encompassed in a protein of unknown function, or into a gene which has not been cloned yet. Therefore, such bioinformatics tools can help to identify functional protein domains which can be expressed by the methods of the invention.

Amongst the commercially valuable functional protein domains, the ones having therapeutic interest represent a preferred group. Most of the therapeutically useful proteins may be grouped into 3 classes: regulatory factors (including hormones, cytokines, lympholines, chemokines, receptors, and other regulatory factors of cellular growth and metabolism), blood products (including serum-derived blood factors and enzymatic fibrinogen activators) and monoclonal antibodies. Primary translational products containing functional protein domains may be encoded by genes belonging to these 3 classes, which can be used as target genes by the methods of the invention to produce functional protein domains using endogenous exons.

However, scientific literature, from which background references and the examples of the present invention have been selected, shows that functional protein domains having therapeutic interest can be identified into primary translational products initially not characterized as belonging to these groups (such as membrane-bound proteins, transmembrane proteins, enzymes, proteins of the extracellular matrix, intracellular signaling and structural proteins, nuclear proteins), but containing as well functional protein domains of therapeutic interest. Therefore, also the genes corresponding to these primary translational products can be used as target genes by the methods of the invention to produce functional protein domains using endogenous exons.

The Host Cell

The invention is generally applicable to protein sequences of eukaryotic origin, since the presence of introns is essentially limited to eukaryotic genes. For this reason, the host cell will typically be a eukaryotic cell, such as a mammalian cell, although other eukaryotic cells derived from plants, insects, yeast and fungi may be used. Provided that most of the functional protein domains of interest belongs to human proteins, human host cells are preferred.

Any eukaryotic cell containing at least a copy of the intron-containing gene coding for the primary translational product containing the functional protein domain of interest can be used, but preferred eukaryotic cells are differentiated and/or immortalized mammalian cells, in particular of human, simian, and rodent origin, like SV40-transformed African green monkey kidney CV1 cells (better known as COS cells), Chinese Hamster Ovary cells (CHO), Human Embyronic Kidney (HEK)-293, Baby Hamster Kidney cells (BHK), Madin-Darby Canine Kidney cells (MDCK) and any other stem, differentiated or indifferentiated eukaryotic cell line where the exon(s) coding for the functional protein of interest are present.

Before being subjected to the methods of the invention, such cells may already be modified at the genomic level with other viral or non-viral constructs, integrated by homologous or non-homologous recombination, which may alter the expression and/or structure of the target gene, or of other genes. In the case of transformed or immortalized cell lines, where more than two copies of the target gene can be present, the regulatory unit can be inserted at one or more of the possible locations by successive rounds of homologous recombination.

The host cell has to be chosen also by taking into account the exogenous regulatory unit integrated at the 5' or 3'end of the relevant exon(s), so that such sequences can fully exert their activity in a constitutive or inducible manner. For example, the methods of the invention may be applied to somatic cell hybrids of immortalized-cells, which can be extremely useful for the expression of specific functional protein domains, in particular for immunoglobulin-derived functional peptides or polypeptides, or for any other functional protein domain whose transcription has been put, using the method of the invention, under the control of immunoglobulin-specific promoter and/or enhancer elements.

Since primary cells can be modified by homologous recombination in culture with frequencies comparable to immortalized cell lines (Hatada S et al., Proc Natl Acad Sci U S A. (2000), 97(25):13807-11), the method of the invention is applicable also to primary cells, whenever the production of the functional protein domain has to be accomplished in a similar cellular environment, for example for gene therapy purposes. Obviously, for the production of a functional protein domain of human origin the host cells will be human cells.

Additional criteria that can be applied for selecting the host cell type for use in the method of the invention are both the inherent capability of the host cell type to allow homologous recombination and the actual transcriptional status of the target gene. A preliminary evaluation of these features amongst the candidate cell types can help choosing the cell type wherein the method can allow a faster and more straightforward isolation of a clone producing the desired functional protein domain.

Homologous recombination frequency has been measured and compared in primate and murine fibroblast cell lines, showing important differences (Taghian D G and Nickoloff J A, Mol. Cell. Biol. (1997), 17(11): 6386-93). Similar assays, based on nuclear extracts and/or transformation with a standard homologous recombination vector, can help to quantify the recombination activity of a specific cell type.

The effect of target gene transcription on gene targeting in cultured human cells has been evaluated by comparing the effects of gene targeting in different loci, in the presence or absence of an agent that stimulates target site transcription (Thyagarajan B et al., Nucleic Acids Res. (1995), 23(14): 2784-90). Gene targeting appears generally to be enhanced by transcription through the target site in a significant way.

Finally, the host cell should express the enzymes that modify posttranslationally the functional protein domain other then the one necessary to generate it from the primary translational product of the target gene. For example, if the functional protein domains correspond to the N-terminus of a secreted primary translational product, the host cell should allow the processing of the signal peptide. In other specific situations, the host cell should allow the correct glycosylation or phosphorylation of the functional protein domain. If a cell type expresses the target gene in cell culture conditions but it does not express the proteolytic activity necessary to generate the functional protein domain, and/or does not express this gene at a level sufficient for commercial exploitation, the methods of the invention permit one to generate clones producing the functional protein domain more efficiently.

The Transcription Module

The transcription module, a first DNA sequence comprised in the exogenous regulatory unit, provides the transcription control elements missing at one end of the targeted exon(s) to obtain a primary transcript comprising, amongst the totality of the exons belonging to the target gene, only the one(s) encoding for the functional protein domain. The transcription module should be integrated in 5' to the more 5' exon, (in the case of a functional protein domain corresponding to the C-terminus of the primary translational product; FIG. 1 A-F), or in 3' to the more 3' exon (in the case of a functional protein domain corresponding to the N-terminus of the primary translational product; FIG. 1 G-L) coding for the functional protein domain.

Depending on the position and on the sequence of the functional protein domain, different kinds of DNA sequences can be included in the transcription module to be integrated in the target gene, oriented in the same direction: promoters, enhancers, recognition sites for transcription factors, polyadenylation sites, and any other kind of DNA sequence able to regulate the transcription of a DNA into an mRNA molecule, including sequences comprised in an intron eventually added in the construct.

Promoters are functionally defined as sites where RNA Polymerase II protein complex starts transcription of a gene. Enhancers and other recognition sites for transcription factors can potentiate promoter activity by interacting with accessory proteins and facilitating the aggregation of an active transcription complex. A promoter, with or without enhancers, is a necessary element of the inserted DNA construct when the functional protein domain is located at the C-terminus of the primary translational product.

The combination of promoter and enhancers preferably used is the one known to promote, constitutively or after induction, the expression of a gene in the host cell line where homologous recombination is performed. For example, if the host cell line consists of pituitary cells which naturally express proteins such as growth hormone and prolactin, the promoter for either of these genes could be used. Also suitable are promiscuous or constitutive DNA regulatory segments that function in most cell types, such as the regulatory elements identified in Rous Sarcoma Virus (RSV), Simian Virus 40 (SV40), Mouse Mammary Tumor Virus (MMTV), Moloney Murine Leukaemia Virus (MoMLV), Cytomegalovirus (CMV), Sindbis (SG). Further examples of promoters are the ones regulating the transcription of human genes like Interferon alpha (IFN-.alpha), Heat Shock proteins (HSP), Elongation factor 1.alpha (EF-1.alpha), Metallothionein-I/-II (MT-I/-II), Ubiquitin C (UbC), Leukosialin (LS). These latter promoters are useful especially when the host cells are highly differentiated, like T-cells (where LS promoter is active).

Inducible promoters are desirable for the production of functional protein domains that, for any reason, may be toxic and/or growth-inhibiting to the host cell. Examples of inducible promoters are MT-I/-II (containing multiple metal response elements active in presence of heavy metals) and Lac (a bacterial operator-repressor system, induced by IPTG, which has been adapted to mammalian cells).

When the functional protein domain is located at the N-terminus of the primary translational product, the transcription module should contain sequences that allow the correct termination and modification of the mRNA at its 3' end, a complex process involving cleavage of the primary transcript and a coupled polyadenylation reaction. The poly(A) tract is present in most mammalian mRNAs, and it is essential for mRNA stability and translation efficiency. The signals for polyadenylation are composed of an AATAAA sequence, located 20-30 nucleotides upstream of the polyadenylation site, and a GT-rich segment, immediately downstream of the polyadenylation-site. There are several efficient poly(A) signals that have been already used in expression vectors and that can be used in the regulatory unit, isolated either in eukaryotic (bovine growth hormone, mouse beta-globin) or viral genes (SV40 early transcription unit, Herpes simplex virus thymidine kinase).

It is evident that, since the level of expression of a gene is mainly determined by the promoter and the other transcriptional regulatory regions in 5' to the gene, the target gene modified with a construct containing transcriptional and translational termination sites has to be already expressed by the host cell at a level considered as sufficient. In these situations, the choice of the host cell has to be directed to cells already strongly expressing the gene coding for the primary translational product.

Associated to poly(A) signal, an additional sequence called the transcription terminator may be present in the transcription module to make sure that transcription does not continue into the 3' adjacent genomic sequence unrelated to the functional protein domain. This event could lead to two possible outcomes: introduction of unnecessary sequence in the primary transcript which could reduce or alter the translation of the desired functional protein domain, and inhibiting the activity of a downstream promoter, which may control a gene important for replication or the metabolism of the host cell. Even if a clear consensus has not been defined by the analysis of several mRNAs, some of these sequences have been well characterized in the literature (Petitclerc D et al., J. Biotechnol.(1995), 40(3): 169-78).

The DNA construct may additionally comprise other DNA sequences that affect transcription. For example, DNA sequences called chromatin opening domains (UCOE), if inserted in proximity to a gene, may allow better expression of a poorly expressed or silent gene by shielding it from putative negative regulatory sequences close to the target gene or by forcing nearby chromatin domains to open. Several of such elements have been reported to increase gene expression from heterologous promoters in tissue-dependent or -independent manner both in transgenic mice or cultured cell lines (WO00/05393).

The Translation Module

The translation module, a second DNA sequence comprised in the exogenous regulatory unit, provides the translation control elements missing at one end of the targeted exon(s) in the correct frame to obtain the correct and efficient translation of the primary transcript into the functional protein domain. The translation module should be integrated between the transcription module and more 5' exon (in the case of a functional protein domain corresponding to the C-terminus of the primary translational product) or the more 3' exon (in the case of a functional protein domain corresponding to the N-terminus of the primary translational product) coding for the functional protein domain, and oriented in the same direction.

Depending on the position and of the sequence of the functional protein domain, different kinds of DNA sequences can be included in the translation module: a translation initiation codon (which, together with the surrounding nucleotide context, forms the Kozak sequence), a translation stop codon, a 5'-/3'-untranslated region, and any other kind of DNA sequence able to regulate the translation of an mRNA into a protein.

A translation initiation codon, which is usually ATG (coding for Methionine), has to be introduced in the translation module whenever the functional protein domain is located at the C-terminus of the primary translational product and the endogenous sequence (either an intron or an exon) does not contain an ATG in a convenient position to be exploited for the correct translation of the functional protein domain. In these situations, the translation module should contain an exogenous ATG codon embedded into a sequence that is comprised in the group of consensus sequences defined by Kozak to have an optimal translation initiation efficiency. Such consensus (CC(A/G)CCATGG) emerged from the analysis of the translation initiation sequence of hundreds of mRNA, but not all nucleotides are equally important: one or more cytosines may be substitutes with another nucleotide but the purine (A/G) must be conserved (Kozak M, Gene (1999), 234(2): 187-208).

The 5' untranslated region (5'UTR), is related to the translation initiation codon since it is the sequence belonging to the primary transcript 5' to the translation initiation codon. Physically, it is the sequence between the transcription initiation site (usually 20-30 nucleotides downstream from the promoter and constituted by a G nucleotide which is modified by the "capping" enzymes) and the translation initiation codon. Depending on the sequence of the intron targeted by homologous recombination and of the adjacent exon coding for the functional protein domain, this sequence can be constituted entirely (if the ATG is also introduced by homologous recombination) or only partially by exogenous sequences. No specific length or consensus sequence for 5' untranslated region has been defined in the literature but, to minimize interferences on the correct and efficient translation of the functional protein domain, it should not exceed 100-200 nucleotides. Moreover, it should not contain additional ATGs or other sequences (such as GC-rich regions) that may pair and create secondary structure which may delay or stop the progression of the ribosome during translation. In certain situations, for example when a 5' UTR is particularly long, an internal ribosomal entry site (IRES) or a translation enhancer element may be incorporated in the 5'UTR to facilitate the interaction of the primary transcript with the ribosomal proteins and increase the translation efficiency, as has been shown for different mRNAs in several mammalian cell types (Liu X et al., Anal Biochem. (2000), 280(1):20-8).

When the functional protein domain is located at the N-terminus of the primary translational product, the translation module should contain sequences that allow the correct termination of translation such as a termination codon and a 3' untranslated region (3'UTR). As mentioned above, depending on the sequence of the intron targeted by homologous recombination and of the adjacent exon coding for the functional protein domain, these sequences can be constituted entirely or partially by exogenous sequence but, in most cases, the translation module will provide both elements. Apart from the well-established stop codon (TGA, TAA, TAG), the sequence surrounding this triplet may have some effects on the efficiency of the termination of translation. If, for example, the nucleotide immediately following the stop codon is an A or G, the termination is more efficient.

As stated for the 5' untranslated region, also for the 3' untranslated region, which consists of the primary transcript segment between the translation stop codon and the polyadenylation site, there is no specific length or consensus sequence described in literature. However, for maximal transcriptional efficiency, it should contain destabilizing regions, like AT-rich sequences.

The translational initiation or termination codon has to be in same reading frame of the functional protein domain encoding sequence. If the intron proximal to the exon(s) encoding the functional protein domain contains a trinucleotide corresponding a stop or to a start codon in the correct frame and at a distance involving the addition of a number of amino acids compatible with the activity of the functional protein domain, the integration of an appropriate transcription module, with a translation module simply containing a convenient untranslated region, can directly allow the correct expression of the functional protein domain. In this way, these trinucleotides and the intronic sequence comprised between them and the more proximal end of the adjacent exon can be fully functional since they become part of this exon.

The peptide sequence that would result, fused at the N- or C-terminus of the functional protein, should not interfere with the functionality of this protein sequence or, if it does, should be easily removed or inactivated during the purification process. In the case of a functional protein domain corresponding to the C-terminus of the primary translational product, the same approach can be also used if the more 5' exon contains an ATG, normally coding for an internal Methionine, in frame with the functional protein domain, limiting its N-terminus. The integration of a transcription module activating transcription 5' to such an ATG should allow the correct transcription and translation of the functional protein domain.

However, the presence of such trinucleotides, which are usually inactive as translational initiation or termination sites since they are either eliminated during splicing (if comprised in an intron) or anticipated by other translational start sites (if comprised in an exon), is limited to a small number of genes. Therefore, translational start or stop codon should be comprised into an exon, either synthetic or natural, which becomes part of the translation module. This module may comprise one or more exogenous exons (separated by natural or synthetic intronic sequences) which may additionally encode for a protein sequence either homologous or heterologous to protein sequences comprised in the primary translational product encoded by the target gene.

However, as in the previous situation, this protein sequence fused to the functional protein should not interfere with the activity of the functional protein domain or, if they are, should be easily removed or inactivated, eventually by enzymatic activities produced by the host cell itself. For example, if the functional protein domain is a C-terminal fragment of a primary translational product, the exon(s) may encode a signal peptide (or the N-terminus of a signal peptide) which, once put in the correct frame between the translational start site and the endogenous exonic sequence, allows the secretion of the functional protein domain in the culture media.

Alternatively, this additional protein sequence may simply be a spacer or linker peptide, which eventually helps the purification and/or collection of the functional protein domain. The additional protein sequence may encode also the recognition-site for a proteolytic enzyme so that, if the functional protein domain can be purified exploiting the affinity of the additional sequence for a substrate immobilized on a support, it can be later eliminated using commercially available proteases.

The Splicing Module.

As noted above, if the endogenous sequence belonging to the target gene does not contain a translation termination or initiation codon in an appropriate position to be exploited (i.e. adjacent or internal to the exon(s) coding for the functional protein domain and having the same frame of the functional protein domain), the construct for homologous recombination will contain one of them into an exogenous exon, either natural or synthetic.

The exogenous exon(s) belonging to the translation module, however, has to be positioned in-frame with the endogenous exon(s). This arrangement can be accomplished either by using a splicing site complementing the splicing site of the more proximal exon (FIG. 1A, D, G, J) or by choosing the targeting sequence in way that the exon is precisely fused to the more proximal exon (FIG. 1B, E, H, K).

Therefore, when the exogenous exon contains a translation start codon, the splicing module will be a 5' donor splice site located at the 3' end of the translation module (FIG. 1A, D), complementing the 3' splice acceptor site associated to the proximal endogenous exon coding for the functional protein domain. Alternatively, when the synthetic exon contains a translation stop codon, the splicing module will be a 3' acceptor splice site located at the 5' end of the translation module (FIG. 1G, J), complementing the 5' splice donor site associated to the proximal endogenous exon coding for the functional protein domain.

The regulatory unit may therefore comprise a splicing module allowing the generation of a transcript coding for a functional protein domain whenever, following the integration of the regulatory unit, residual intronic sequences separate the translation module from the exon(s) coding for the functional protein domain. The endogenous splicing sequences that usually drive the fusion of the exon(s) other than the ones coding for the functional protein domain to the one(s) put under the control of the exogenous regulatory unit, should be unable to reconstitute the splicing events of the target gene in the host cell. This is due to the fact that the regulatory unit replaces them and/or is positioned in a way that they are too far away and cannot exert their activity efficiently, remaining unpaired.

The 5'/3' splice sites are fundamental elements for the expression of a gene, since they enable the proper splicing of the primary transcripts generated from intron-interrupted gene. These sequences are well conserved in many vertebrate genes, especially at the 5' and 3' end of introns. Most of the 5' splice donor sites in higher Eukaryotes conforms to the consensus sequence AG][GTRAGT, where AG is the conserved dinucleotide motif at $\overline{3'\text{end}}$ of the exon, ][ denotes the splice site, GT is the highly conserved dinucleotide motif at 5'end of the $\overline{\text{intron}}$ and R is a purine. A 3' splice acceptor site is constituted essentially by the consensus sequence YAG][G, where AG is the highly conserved dinucleotide motif $\overline{\text{at 3'}}$end of the intron (typically preceded by a stretch of pyrimidine (Y)), ][ denotes the splice site, and G is a conserved nucleotide at the 5' end of the exon.

Apart from the appropriate consensus splicing sequence, the splicing module is followed by intronic sequences which come from the adjacent targeting region, by natural or synthetic intronic sequences added in the construct between the splicing site and the targeting region. Such intronic sequences may contain, for example, another sequence element known as the branch site, which is usually located at a distance of 18-40 nucleotides upstream of the 3' splice site. This site displays the sequence CTRACT, where N is any nucleotide and A is the nucleotide that has a —OH group capable of interacting with phosphate group of the G nucleotide at the 5' end of the intron during the catalytic steps of mRNA splicing. The consensus sequences, the mechanism, the factors and other regulatory sequence involved in mammalian pre-mRNA splicing, like the exonic splicing enhancers, have been reviewed (Long M et al., Proc. Natl Acad. Sci USA, (1998), 95(1): 219-223; Blencowe B J, Trends Biochem. Sci. (2000), 25(3):106).

The advances in the knowledge of splicing mechanisms, even though not allowing a more precise definition of general consensus sequences, may lead to a selection of specific splicing modules in relation to the cell type to be modified by homologous recombination. For example, a series of sequence features and motifs has been found to be common to brain-specifically spliced genes, indicating that a regulation of cell type-specific splicing can be possible by selecting such sequences (Brudno M et al., Nucleic Acids Res. (2001), 29(11): 2338-48).

The splicing module is separated from the endogenous splicing control element, present at the proximal end of the adjacent exon coding for the functional protein domain in the target gene, by an intron containing sequences which can be entirely endogenous, entirely exogenous or a hybrid of endogenous and exogenous sequences. Since this sequence will ultimately be spliced out, the precise sequence may not matter, as long as it does not adversely interfere with the proper expression of the desired functional protein domain.

The DNA Targeting Sequence

The DNA targeting sequence is an essential element of the construct since it is responsible of the correct integration and positioning of the exogenolis sequences (regulatory unit, positive marker gene) in the genome of the cell. Such sequences, usually cloned or PCR-amplified from genomic DNA, are defined functionally as having a level of homology with endogenous DNA sufficient for driving the molecular processes causing homologous recombination (strand pairing and displacement) in a specific genomic region.

The DNA targeting sequence may be constituted by a single DNA segment or divided in two DNA segments, separated in the construct by the exogenous sequences corresponding to the regulatory unit and, eventually, by the positive marker gene. While two targeting segments are preferred in order to increase the efficiency and the precision of the integration, the present invention also comprehends the use of a single targeting segment. In its simplest form, a circular piece of DNA is employed which contains the regulatory unit along with the targeting segment. In this way, the homologous targeting segment hybridizes with its genomic counterpart and the regulatory unit is inserted within the target gene following the crossover event.

The size of each of the targeting segments (i.e. the regions of homology) is not critical, although the shorter the regions are, the less likely that they will find the appropriate regions of homology and recombine at the desired spot. Thus, the shorter the regions of homology, the less efficient is the homologous recombination, i.e., the smaller the percentage of successfully recombined clones. It has been suggested that the minimum requirement for sequence homology is 25 base pairs (Ayares D et al., Proc Natl Acad Sci U S A. (1986), 83 (14): 5199-203). Optimum results are achieved when the total region of homology, including both targeting regions, is large, for example one to five kilobases or more. As long as the regulatory unit can be introduced at the appropriate point in the genome, there is no limit to the size of the targeting segments, if it does not affect vector stability.

The DNA targeting sequences will contain, in many situations, the complete, or a segment of the, intron 5' (if the functional protein domain is at the C-terminus of the primary translational product) or 3'(if the functional protein domain is at the N-terminus of the primary translational product) of the exon(s) coding for the functional protein domain (FIG. 1A, D, G, J). The targeting region may include other parts of the target gene, including the exon(s) encoding the functional protein domain, in addition to this specific intron (FIG. 1B, E, H, K). In some other cases, the intron(s) and the exon(s) proximal to the exon(s) coding for the functional protein domain can be more or less completely removed and substituted by the exogenous regulatory unit (FIG. 1C, F, I, L), eventually by making use of sequence located in a contiguous gene. If the DNA targeting sequence is constituted by a single DNA segment, it should be homologous to a segment of the target gene comprised only in the portion of the target gene including the exon(s) coding for the functional protein domain, to a segment of the target gene comprised only in the portion of the target gene including the intron proximal to the exon(s) coding for the functional protein domain, or to a segment of the target gene including sequences belonging to both these regions. In any case, the integration of the construct within the host cell genomic DNA by homologous recombination at a position determined by the DNA targeting seg-ment(s) should allow expression of the functional protein domain under the control of the regulatory unit.

Such targeting strategies are feasible, as long as the integration of the construct will not lead to any modification of the order and/or sequence of genomic elements coding for the functional protein domain or of other genomic sequences that are necessary for cell viability or metabolism. If the primary translational product of the target gene itself is essential for cell viability or metabolism, the copy of such gene not modified by homologous recombination should usually have an expression level sufficient for keeping the cell metabolically active.

The knowledge of the complete gene sequence and structure, from the promoter to the polyadenylation site, helps choosing the more appropriate targeting strategy, but it can be possible to generate the construct just starting from the sequence and the structure of the exons and introns associated to the functional protein domain. This can happen in particular for the human genes for which it is available only a genomic clone containing good candidate sequence for the 5' or 3' end, in particular when compared to corresponding mouse gene already sequenced and characterized. On the basis of homology with other genes in the same or other organisms and of computer predictions (Rogic S et al., Genome Res. (2001), 11(5): 817-32), the relevant exon/intron junctions, together with the surrounding sequences limiting at one end the functional protein domain, can be defined on the genomic clone. Therefore, fragments of the genomic clone can be selected since they have a length sufficient for generating the targeting sequences necessary for guiding the regulatory unit in the correct genomic location.

The DNA targeting sequence may contain sequences homologous to the target gene which are either contiguous or non-contiguous in the targeted genome. In the first case, there will be the simple insertion of the exogenous sequence, either internally or at one end of the intron proximal to the exon(s) coding for the functional protein domain (FIG. 1A, B, D, E, G, H, J, K). In the second case, the portion of the target gene separating the non-contiguous sequences proximal to the exon(s) coding for the functional protein domain (intron (s) and/or exon(s)) will be deleted and replaced by the exogenous sequences as a consequence of the homologous recombination (FIG. 1C, F, I, L). In both types of vectors, homologous recombination is driven by DNA sequences of the incoming, exogenous DNA which can be aligned directly with homologous sequences in the target gene coding the functional protein domain. The particular linear arrangement of the homologous sequences in the exogenous DNA will determine the position and the orientation of the regulatory unit at the level of the intronic region proximal to the exon(s) coding for the functional protein domain.

Whenever the targeting segments are obtained by PCR and/or derive from a cell non-isogenic with the host cell, they should be sequenced when preparing the construct to identify any sequence difference (due to the origin of the targeting region) which may significantly alter the expected sequence and expression of the functional protein domain.

While the type of targeting construct chosen will determine the nature of the genomic modification of the target gene resulting in a recombinant gene encoding a functional protein domain, the actual efficiency with which a given construct can be used to obtain targeted cell lines depends primarily on the targeting construct.

In particular, the absolute targeting frequency that can be achieved with the construct has been shown to depend on a number of factors, including the length of the homologous sequences in the targeting construct, the degree of homology between the sequences in the targeting construct and the target gene, and the particular genomic region being targeted. Targeting frequency has been shown to increase as the length of sequence homology between the targeting vector and the locus increases, until a plateau in targeting frequency is reached between 10-14 kb, with no consistent difference in frequency between the insertional and replacement vectors (Deng C and Capecchi M R, Mol Cell Biol. (1992), 12(8): 3365-71.). This plateau may reflect a limit on the size of intact DNA fragments that can be introduced into the cells, rather than a limit in the effect of length of homology on targeting frequency.

Regarding the level of homology required to drive the correct integration of the construct by homologous recombination, the DNA targeting sequence must hybridise with endogenous sequences at the stringent hybridization conditions described in the literature (Sambrook et al., "Molecular Cloning: A Laboratory Manual", Cold Spring Harbor Press, 1989), for example using the following wash conditions: 2×SCC, 0.1% SDS, room temperature twice, 30 minutes each; then 2×SCC, 0.1% SDS, 50 C once for 30 minutes; then 2×SCC, room. temperature twice, 10 minutes each.

Homologous sequences can be identified that contain at most about 25-30% base pair mismatches. More preferably, homologous nucleic acid strands contain 15-25% base pair mismatches, even more preferably 5-15% base pair mismatches. These degrees of homology can be selected by using more stringent wash conditions for identification of clones from gene libraries (or other sources of genetic material), as is well known in the art.

The Selectable Marker Gene

The construct may also comprise one or more of a positive selection gene, an amplifiable gene and a negative selection gene. The construct used for the homologous recombination may contain exogenous sequences other than the ones constituting the regulatory unit In particular, one or more of a positive selection gene, an amplifiable gene or a negative selection gene may be added to the construct to facilitate the identification of the transformed clones having the regulatory unit integrated correctly in the genome. For this reason, the amplifiable and/or marker gene(s) are positioned in the construct between the targeting regions, usually between the transcription module and one of the targeting regions (FIG. 1D-F, J-L). Whatever selectable marker gene is used, it should constitute a transcriptional and translational unit distinct from the one of the functional protein domain and, to avoid any interference with the latter one, it can be separated from the regulatory unit by sequences that avoid any "read-through" event, such as the transcription terminators described previously. Eventually, the positive marker gene can lack transcription and/or translation signal sequence at one end, and that will be provided by the target gene only when properly integrated, generating a fusion gene.

A positive selectable marker gene is capable of rendering the transfected host cell resistant to a normally toxic environment. Examples of such genes are adenosine deaminase (ADA), aminoglycoside phosphotransferase (neo), dihydrofolate reductase (DHFR), hygromycin-B-phosphotransferase (HPH) thymidine kinase (tk), xanthine-guanine phosphoribosyltransferase (gpt), multiple drug resistance gene (MDR), ornithine decarboxylase (ODC) and N(phosphonacetyl)-L-aspartate resistance (CAD).

In addition, or as an alternative, to the positive selectable marker gene, an amplifiable gene can also be optionally included in the construct. Amplifiable genes are genes that lead to an increase in copy number when under selective pressure The copy number of a gene positioned adjacent to the amplifiable gene, including the novel gene encoding the functional protein domain, will also increase. Amplifiable genes that can be used include DHFR, MDR, ODC, ADA and CAD. The members of the positively selectable marker gene group and those of the amplifiable gene group overlap so that, in theory, instead of using two genes, one for positive selection and one for amplification, one gene could be used for both purposes. However, since most cell lines contain endogenous copies of these amplifiable genes, the cells will already be somewhat resistant to the selection conditions and distinguishing the cells which have transfected DNA from those which do not receive transfected DNA can be difficult. Thus, in instances where an amplifiable gene is desired, a positive selection gene which is dominant, such as HPH, gpt, neo and tk (in tk⁻ cells), should also be included in the construct. For some applications it may be possible or preferable to omit the amplifiable marker, even if an increase of the copy number of the novel gene coding for the functional protein domain may finally provide a larger amount of this protein. Amplification may not be necessary, for example, when the regulatory unit drives the trnnscription and the translation of the functional protein domain very efficiently. It is also possible to eliminate the positive selection gene and select cells solely by screening for the production of the desired protein or mRNA. However, it is preferred in most cases to include at least the positive selection gene.

A negative selectable marker gene may also be present in the construct, externally to the targeting sequences. Such a gene is not expressed in cells in which the DNA construct is properly inserted by homologous recombination since it is eliminated, but is expressed in cells in which the DNA construct is inserted improperly, such as by random integration. If the vector inserts correctly by homologous recombination, it will recombine in the regions of homology, causing the loss of sequences outside of those regions. One such gene is the Herpes Simplex Virus thymidine kinase gene (HSVtk). The HSVtk has a lower stringency for nucleotides and is able to phosphorylate nucleotide analogues that normal mammalian cells are unable to phosphorylate. If the HSVtk is present in the cells, nucleotide analogs such as acyclovir and gancyclovir are phosphorylated and incorporated into the DNA of the host cell thus killing the cell.

Whatever marker gene is used, it is well recognized in the literature that such gene can be removed subsequently by using a site-specific recombinase (like Flp or Cre), already present in the cell genome, co-transfected with the construct for the homologous recombination, or introduced afterwards by transformation or any recombinant technology. Such procedures, which may be necessary if the marker gene affects the transcription of the nearby genes, have been described and it can be eventually used for activating or inactivating elements of the regulatory unit (Gorman C and Bullock C, Curr Opin Biotechnol (2000), 11(5):455-60; Kuhn R and Schwenk F, Curr. Opin. Immunol. (1997), 9(2): 1838).

The Construct

The construct, or targeting vector, comprising the DNA sequences, as previously described, is introduced, in a linearized or circular form, into a host cell, so that the DNA targeting region can hybridize with the homologous genomic sequence and allow the homologous recombination between endogenous and exogenous sequences, which are stably integrated in the genome of the host cell.

The assembly of the construct should take into consideration the orientation of the exon(s) coding for the functional protein domain. Thus, the targeting sequence should be cloned in the construct to allow the elements comprised in the regulatory unit to be integrated by homologous recombination in the same orientation, determining the operative link between the exogenous regulatory unit and the endogenous genomic region comprising the exon(s) coding the functional protein domain. On the contrary, selectable marker gene(s) may have any orientation but, as said before, they should not interfere with the activity of the exogenous regulatory unit, and therefore are usually positioned the transcription module and the more proximal targeting sequence (FIG. 1D-F, J-L). DNA sequences belonging to the construct other than the regulatory unit and the selectable marker gene(s), which may be eventually integrated by homologous recombination (related to the replication or selection in bacterial cells, for example), should also not affect the transcription or translation of the functional protein domain.

Production of a Functional Protein Domain

Once the amino acid sequence and gene structure of a functional protein domain is known, its production can be obtained using the methods of the invention using the following procedure:

- Identification of the target gene region in which the integration (either by insertion or by replacement) of the regulatory unit will allow the precise and efficient expression of the functional protein domain;
- Construction of the targeting vector, containing the targeting sequences, the regulatory unit and, optionally, amplifiable and/or selectable marker gene(s);
- Selection of a convenient host cell, containing the targeting sequences and the exon(s) coding for the functional protein domain;
- Transformation of the host cell with the construct using known techniques (lipofection, electroporation, calcium phosphate precipitation);
- Identification of the transformants containing the recombinant gene as expected after homologous recombination, using technologies like positive and/or negative selection, amplification, restriction sites analysis, genomic/reverse transcription PCR, Southern blot, or DNA sequencing;
- Expansion of the selected transformants and selection of the clones expressing correctly the functional protein domain, applying techniques of mRNA analysis (primer extension, Northern blot) and protein analysis (Western blot, ELISA, protein sequencing, epitope mapping, two-dimensional polyacrylamide gel, affinity purification, enzymatic assays, CD/NMR spectrum analysis, HPLC gel filtration, Mass Spectrometry) on samples collected and processed from the cultured cells and/or the culture medium using common separation technologies (cell lysis/disruption, extraction, precipitation chromatography);
- Further expansion of the selected clones in culture to allow a quantitative analysis to choose the homologously recombinant clone useful for commercial production and to develop an efficient protocol for expressing and purifying the functional protein domain collected from the expanded cell cultures.

The DNA constructs can drive the insertion of the regulatory unit and, optionally, of a marker gene in the intronic region adjacent to the exons coding for the functional protein domain, so that the transcription and the translation of the functional protein domain is started (as represented in A-F by ⟶) or stopped (as represented in G-L by the symbol ⊣). Endogenous and marker gene transcriptional/translational start and stop regulatory elements are symbolically represented by → and ⊣, respectively.

The splicing module can be located at the 3' end (A and D) or at the 5' end (G and J) of the translation module. For example, if the insertion of the exogenous regulatory unit divides the intron (IN2) in two parts (IN2' and IN2"), the intervening intronic sequences (IN2" in A and D; IN2' in G and J) are spliced out by making use of the splicing module, so that EX3/EX4 (in A and D) or EX1/EX2 (in G and J) are selectively transcribed and translated to obtain the functional protein domain. Alternatively, the DNA constructs may drive the insertion of the regulatory unit and, optionally, of a marker gene between the intron and the exon of interest (IN2 and EX3 in B and E; IN2 and EX2 in H and K), without dividing the intron, so that EX3/EX4 (in B and E) or EX1/EX2 (in H and K) are selectively transcribed and translated to obtain the functional protein domain.

Figure 1:
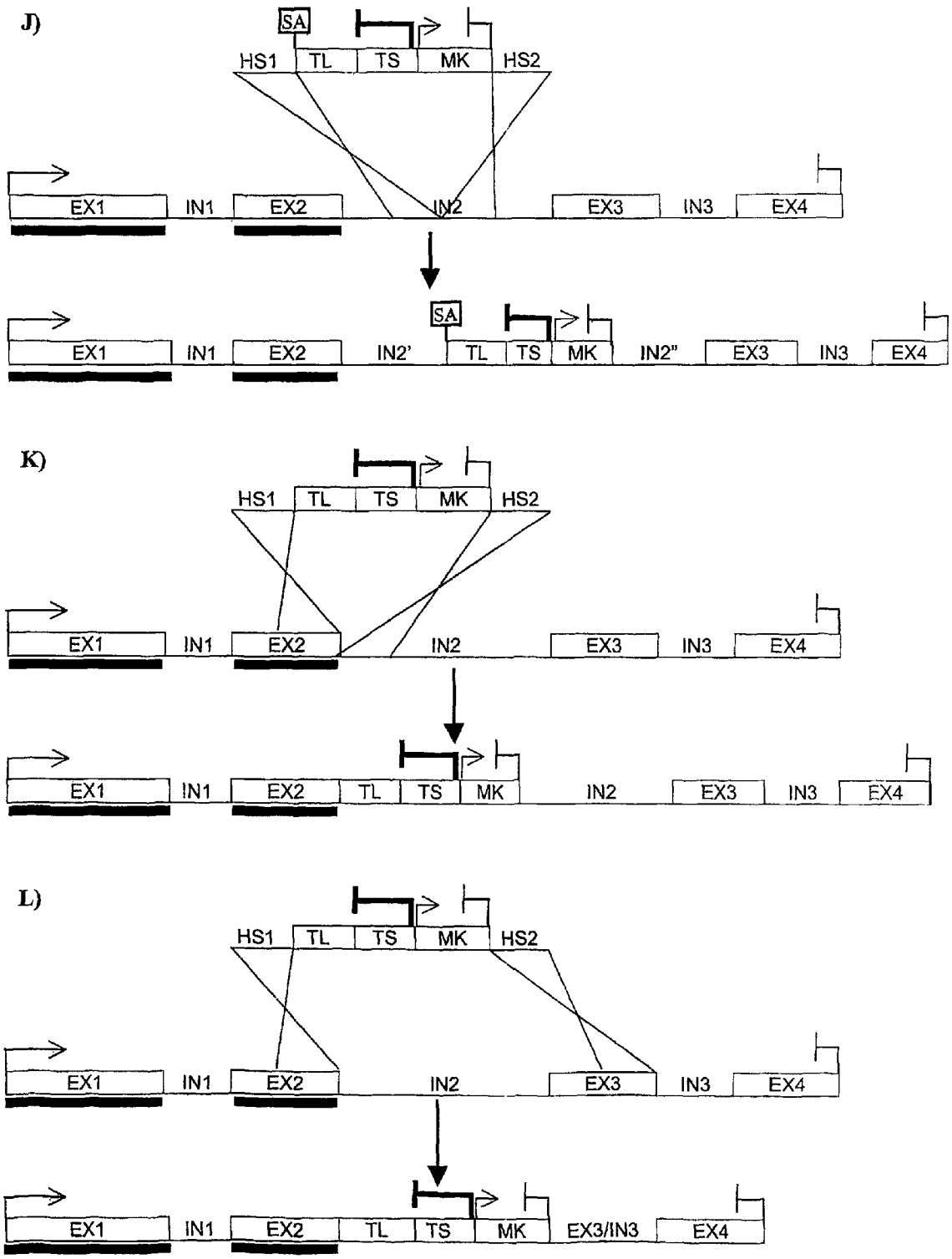
FIG. 1 shows some possible ways that a DNA construct of the invention can homologously recombine with a target gene to obtain a novel gene expressing the exons coding for a functional protein domain. HS1 and HS2 are the construct segments homologous to the target gene containing the exons coding for the functional protein domain, which are used as DNA targeting sequences. In this schematic representation, the target gene contains 4 exons (EX1, EX2, EX3, EX4) and three introns (IN1, IN2, IN3). The exons coding for the functional protein domain are the ones indicated with a black bar, and located either at the 3'end (in A-F) or at the 5'end (in Q-L) of the target gene. In D-F and J-L, the construct contains also a marker gene (MK). The regulatory unit is composed by the transcription module (TS) and the translation module (TL), and, whenever it is necessary to splice out intronic sequences between the translation module and the more proximal exon coding the functional protein domain, an exogenous splicing module which contains either a splicing donor site (SD in A and D) or splicing acceptor site (SA in G and J).

Still alternatively, the DNA constructs may drive the replacement of an endogenous gene segment adjacent to the exons coding for the functional protein domain with the exogenous regulatory unit and, optionally, of a marker gene. Like in the previous situation, one targeting sequence belongs necessarily to an exon coding for the functional protein domain (EX3 in FIGS. 1B, C, E, and F; EX2 in FIGS. 1H, I, K, and L), while the other targeting sequence corresponds to endogenous sequence not comprised in the genomic region for the functional protein domain. The result is the replacement of the segment between the two homology regions (IN2 and part of EX2 in FIGS. 1C and F; IN2 and part of EX3 in FIGS. 1I and L) with the exogenous regulatory sequence, while new intronic sequences are generated (IN1/EX2 in FIGS. 1C and F; EX3/IN3 in FIGS. 1I and L).

Figure 2:
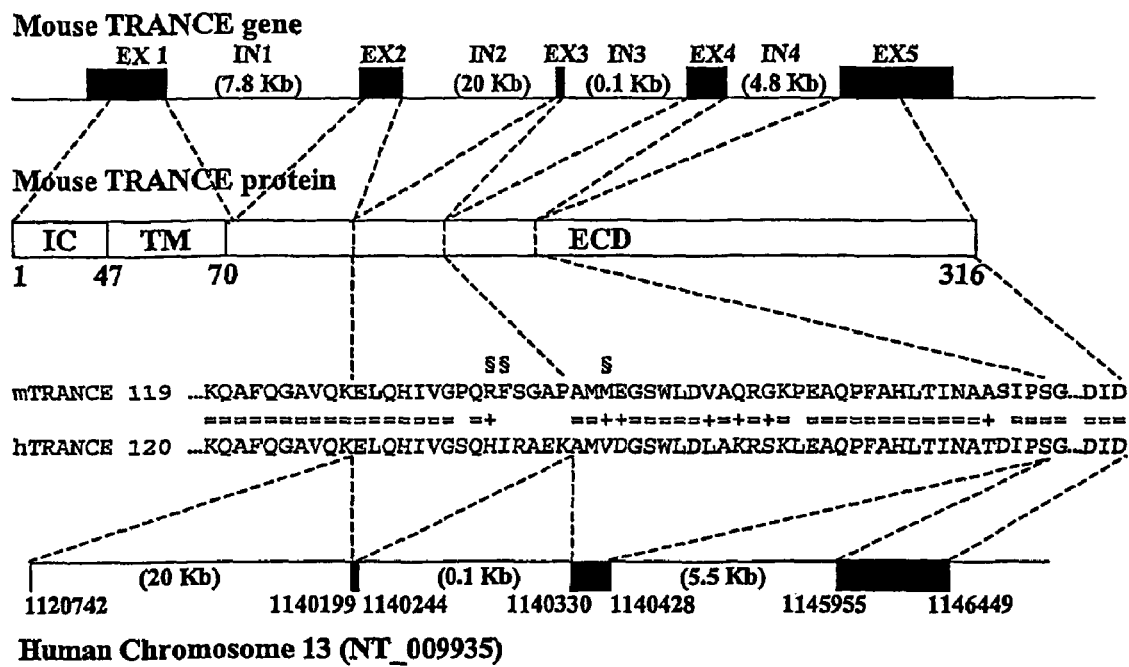

FIG. 2 shows an alignment of mouse and human TRANCE protein (with partial mouse sequence SEQ ID NO: 1 and partial human sequence SEQ ID NO: 2 being aligned and shown) in the region proteolytically processed to generate sTRANCE (= means identity, + means homology). The residues known as possible N-terminus of mouse sTRANCE (Schlondorff J et al., *J Biol Chem.* (2001), 276(18):14665-74) are indicated with §. The correspondence amongst sTRANCE N-terminus, mouse TRANCE protein (IC, TM, and ECD stand for intracellular, transmembrane, and extracellular domain, respectively), mouse TRANCE gene (EX stands for exon, IN for intron, followed by the relative number), and human chromosome 13 (nucleotide numbering is relative to the GenBank version NT_009935.3) is indicated with the dotted lines. The numbering of human and mouse protein sequences corresponds to the original publications (Anderson DM et al., Nature (1997), 390(6656):175-9; Wong BR et al., *J Biol Chem*. (1997), 272 (40):25190-4).

Figure 3:
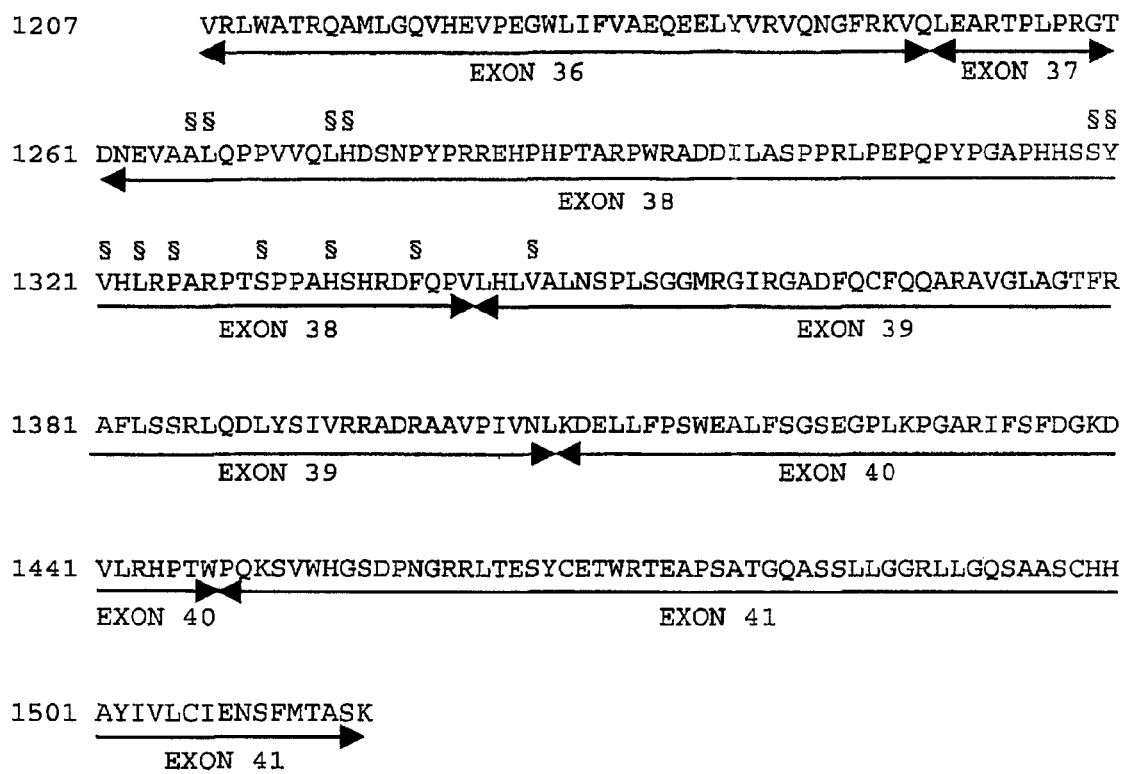

FIG. 3 shows the protein sequence of the human collagen XVIII 1alpha NC1 domain with the corresponding encoding exons (SEQ ID NO: 3). The numbering corresponds to the complete long variant sequence as published (Oh SP et al., Genomics. 1994 February;19(3):494-9). Residues characterized in literature as possible N-terminus of functional protein domains of mouse or human endostatin are indicated with §.

FIG. 4.(A) shows the position of the 5' and 3' targeting sequence used for constructing pEnd-HR#1 and pEnd-HR#2 on human COL18A1 gene. The primers designed for amplifying the COL18A1 genomic sequences necessary for constructing the targeting vectors using the original AL163302 GenBank clone, the length of the exons and of the amplified sequences are also indicated. (B) shows a simplified representation of pEnd-HR#1 and pEnd-HR#2 indicating the relative position of the regulatory unit, of the targeting sequences (dotted lines), and of positive and negative marker genes. The box shows the sequence coding for the mouse Ig Signal Peptide (mIgSP; nucleotides 1-56 of M13329 GenBank record), followed by the splicing donor site (SD; underlined sequence) including the last nucleotide of this coding sequence and the first six nucleotide of the intron, chosen amongst the motifs stimulating splicing (SEQ ID NO: 4). The splicing site is indicated with the symbol ][. The original mouse Ig Signal Peptide last codon TCA was modified to TCG to provide a better 3' end of the mIgSP exon for its correct splicing but this mutation does not change the corresponding amino acid (Serine).

Figure 5:
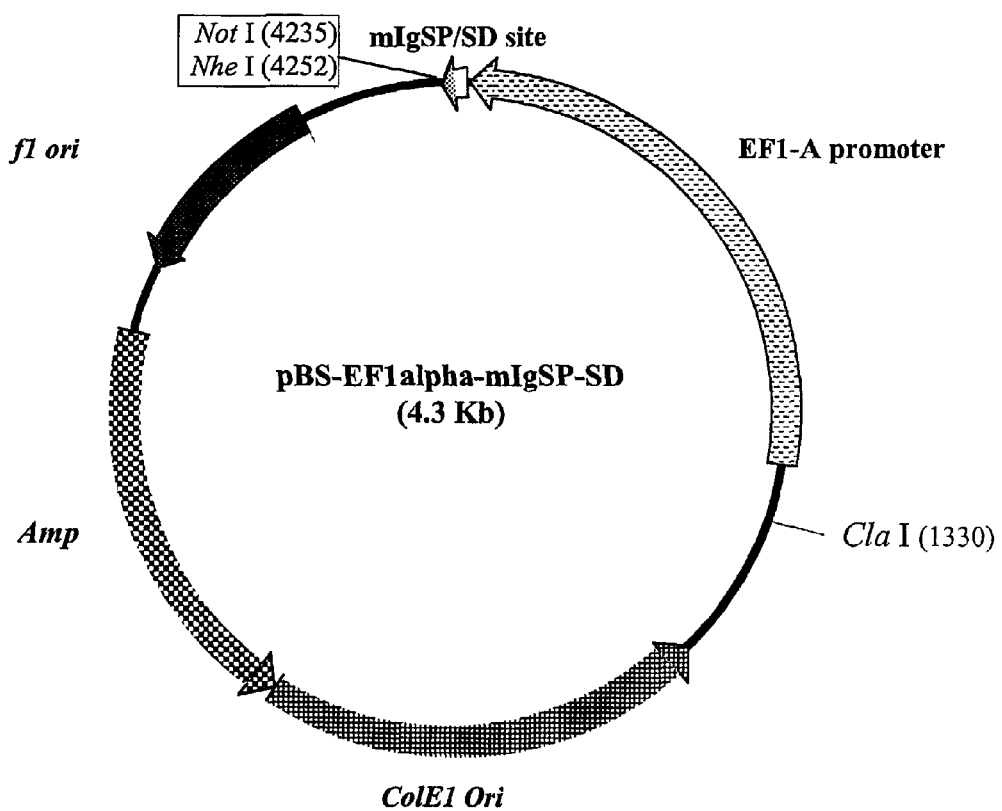

FIG. 5 shows a simplified map of the plasmid pBS-EF1alpha-mIgSP-SD with relevant restriction sites.

Figure 6:
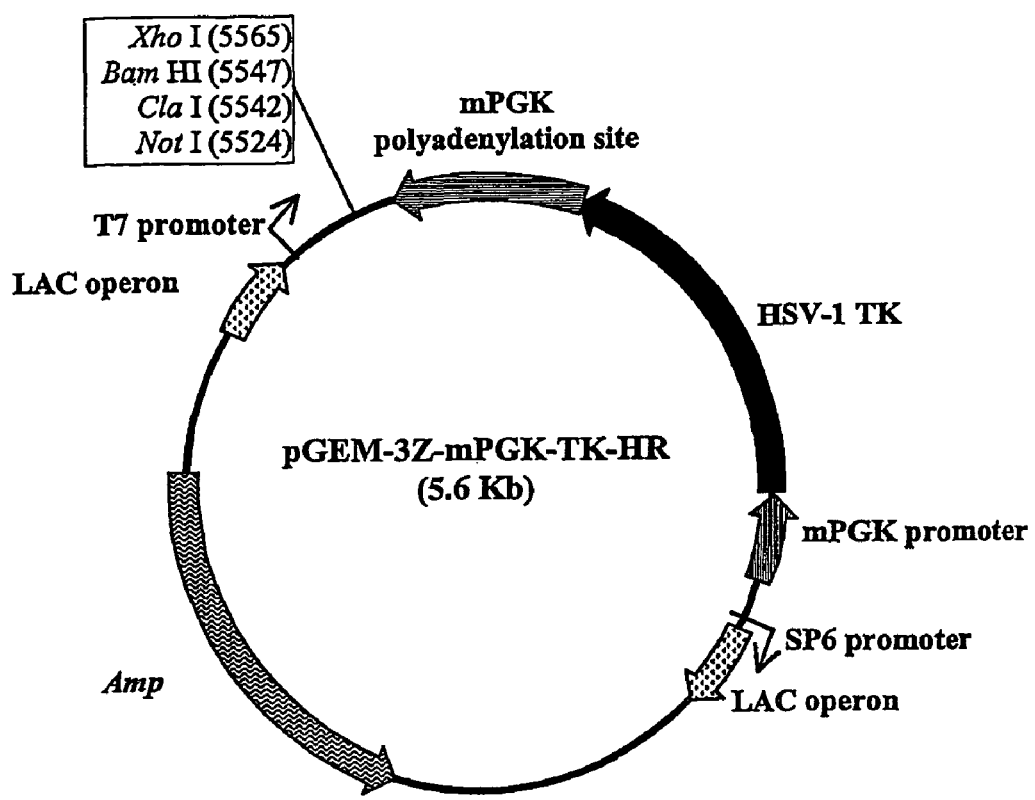

FIG. 6 shows a simplified map of the plasmid pGEM-3Z-mPGK-TK-HR with relevant restriction sites.

Figure 7:
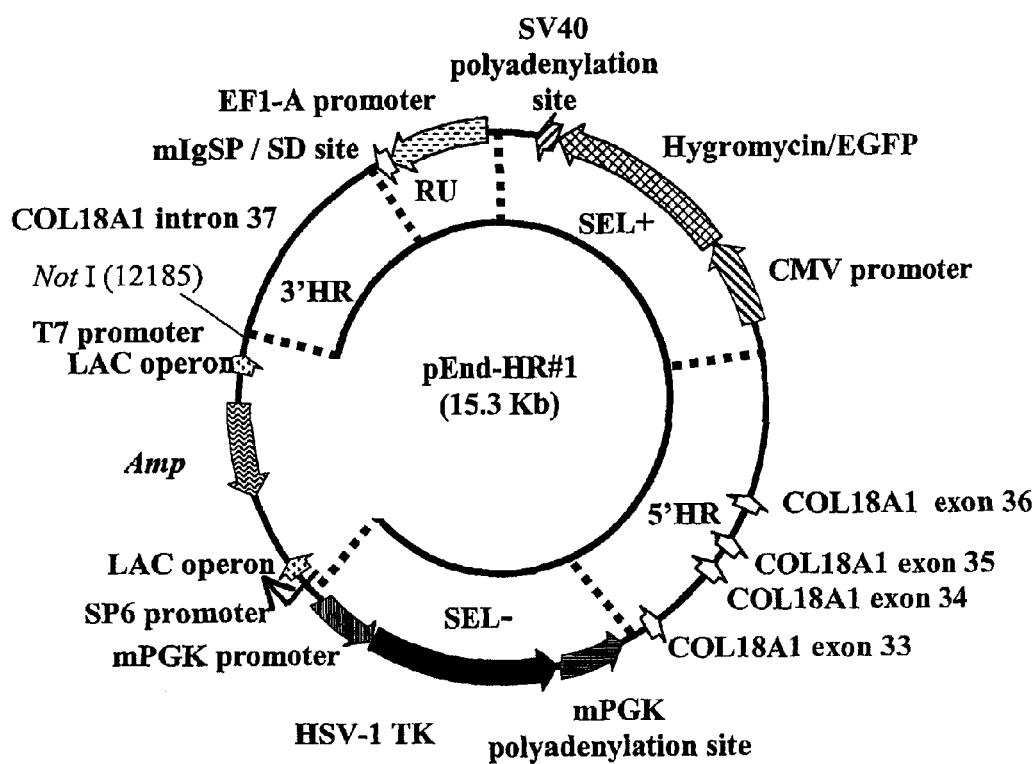

FIG. 7 shows a simplified map of the plasmid pEnd-HR#1. It also indicated the relative position of the 5' and 3' targeting regions (5'HR and 3'HR), of the genes for positive selection (SEL+) and for the negative selection (SEL−), and of the regulatory unit (RU) containing the EF1-alpha promoter, the mouse Ig signal peptide, and the splice donor site. The NotI unique restriction site used for linearizing the plasmid prior to transfection is located at the end of 3'HR. The plasmid pEnd-HR#2 differs by pEnd-HR#1 at the level of length and position on the genomic DNA of the targeting sequences (FIG. 4A), and it is slightly larger (16.9 Kb).

FIG. 8 shows the sequence of the novel mRNA expressed in cells wherein the plasmid pEnd-HR#1 is correctly integrated in human COL18A1 gene, in particular the mIgSP exon and the endogenous coding sequences. Start and stop codons are indicated in bold. The complete mRNA contains 2210 nucleotides (only the coding part of exon 41 is shown as SEQ ID NO:5), while the functional protein domain is encoded as a protein containing 275 amino acids (SEQ ID NO:6; 19 of them belonging to mIgSP exon, and 256 of them belonging to human COL18A1 exons 38-41 coding sequence).

FIG. 9 shows the sequence of the novel mRNA expressed in cells wherein the plasmid pEnd-HR#2 is correctly integrated in human COL18A1 gene, in particular the mIgSP exon and the endogenous coding sequences. Start and stop codons are indicated in bold. The complete mRNA contains 1964 nucleotides (only the coding part of exon 41 is shown as SEQ ID NO:7), while the functional protein domain is encoded as a protein containing 193 amino acids (SEQ ID NO:8; 19 of them belonging to the mIgSP, and 174 of them belonging to human COL18A1 exons 39-41 coding sequence).

FIG. 10.(A) shows a simplified map of a pEAK-HR#2 fragment. The COL18A1 intron 37 and coding sequences of exons 39-41 were fused to a FLAG epitope and to a polyadenylation site. The pEAK-HR#1 contained intron 37 instead of intron 38, and exon 38 between intron 37 and exons 39-41. (B) shows a Western blot performed using whole cellular extracts tested with a rabbit polyclonal antibody against human endostatins diluted 1/100 (Chemicon AB 1878). (C) shows a Western blot performed using 1.5 milliliter of conditioned medium from the same transfected cells tested by immunoprecipitation with a mouse monoclonal anti-FLAG-M2 antibody diluted 1/1000 (Sigma F3165) and 20 microliters of M2-FLAG-agarose (Sigma A1205). Secondary antibody linked to Horseradish peroxidase labeled antibodies against either goat anti-rabbit or anti-mouse were diluted 1/10000 (Amersham-Pharmacia) and detected with the ECL Western Pico reagent (Pierce). The expected molecular weight for the functional protein domains for pEnd-HR#1 and pEnd-HR#2 is respectively 31 Kd and 22 Kd (prior to signal peptide elimination, as in B) or 29 Kd and 19 Kd (after elimination of the signal peptide and secretion in the culture medium, as in C). The shift in molecular weight is due to glycosylation at the level of the sequence encoded by exon 38.

FIG. 11.(A) shows a simplified map of the 1.0 Kb long coding region contained in the expressed by human 293-EBNA cells following the integration of pEnd-HR#1. The position of the primers used to identify the transcript is indicated. (B) shows a simplified map of the 2.4 Kb long COL18A1 genomic region in human 293-EBNA cells following the integration of pEnd-HR#1. The position of the primers and restriction sites used to characterize the clones is indicated.

Figure 12:
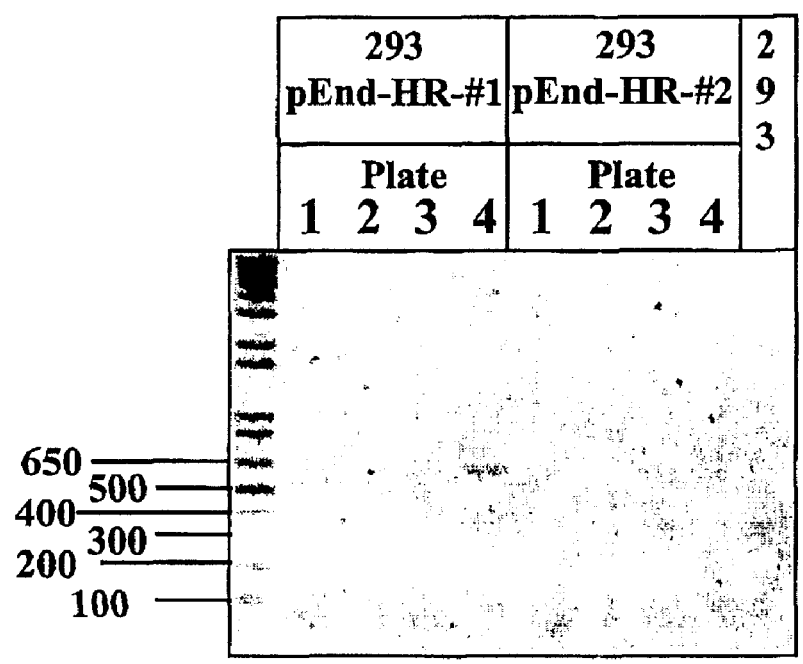

FIG. 12 shows an agarose gel where the amplification products, obtained by amplifying cDNA of the selected cells with o-1165 and o-1175 as primers, are separated. Each pool corresponds to cells obtained from a single plate.

Figure 13:
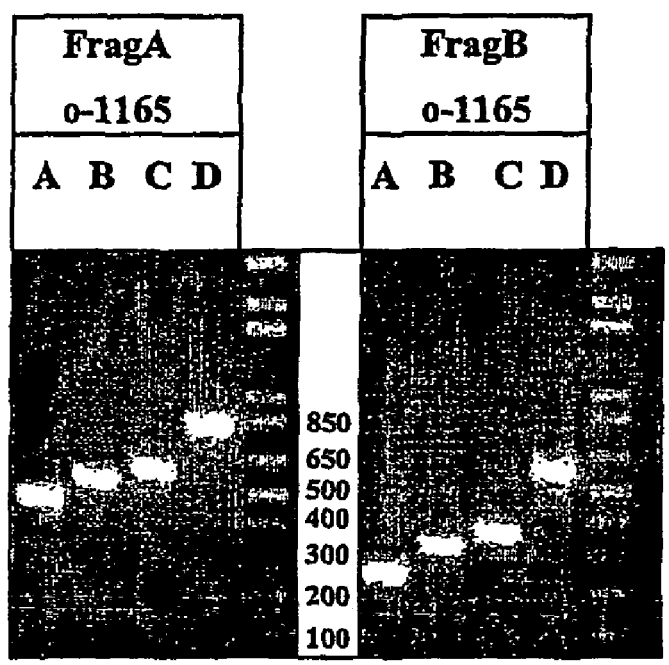

FIG. 13 shows the restriction analysis of the two amplified segments obtained from the pool 4 of pEnd-HR#1 positive clones, FragA and FragB. The expected length of the amplified fragments obtained from FragA are 501 (A), 577 (B), 618 (C), and 851 (D) bases. The expected length of the amplified fragments obtained from FragB are 255 (A), 331(B), 372 (C), and 605 (D) bases.

FIG. 14.(A) shows the DNA fragments amplified using o-1165 and o-1166 exon-specific primers using either genomic DNA extracted from original pool 4 of 293-EBNA cells transfected with pEnd-HR#1 (1), from pools of clones further isolated from this latter pool (2-4) or from untransfected 293-EBNA cells (5). (B) DNA fragments amplified using o-1121 and o-1168 intron-specific primers using either genomic DNA extracted from different pools of clones isolated from the original pool 4 of 293-EBNA cells transfected with pEnd-HR#1 (2-4) or from untransfected 293-EBNA cells (5). The pools of clones in lanes 2- 4 still express the expected transcript.

Figure 15:
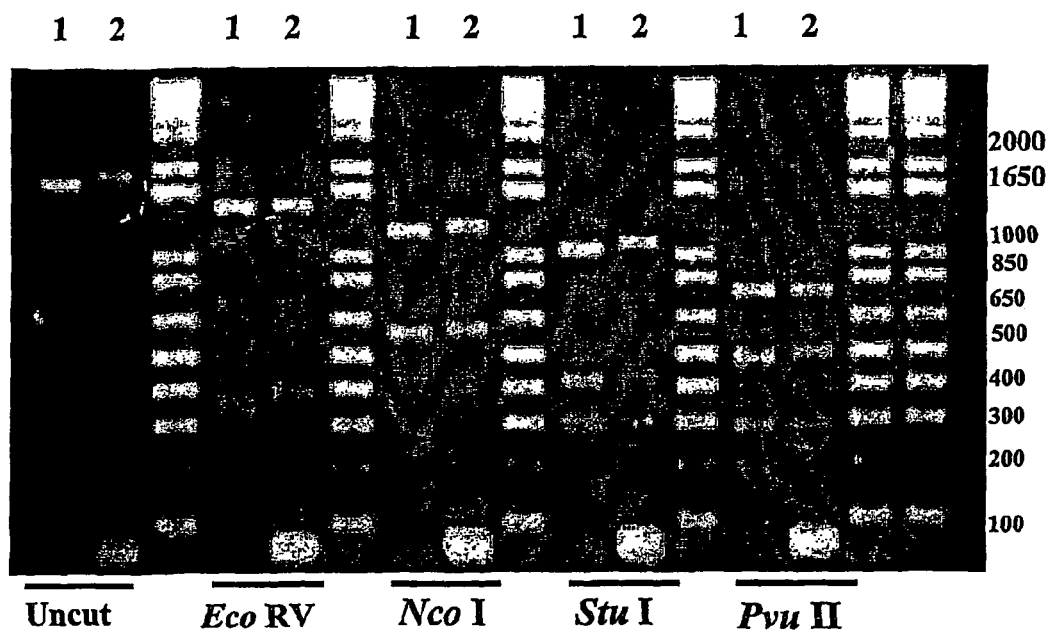

FIG. 15(A) DNA fragments amplified using either genomic DNA from 293-EBNA cells and primers specific either for sequences present in intron 37 (1), or genomic DNA from pEnd-HR#1 positive pool of clones, previously identified by RT-PCR, and primer hybridizing in mIgSP exon and exon 38 (2), together with the pattern obtained from each of the two fragments with a series of restriction enzymes. (B) Table summarizing the expected length of the DNA fragments.

The invention will now be described with reference to the following examples, which should not be construed as in any way limiting the invention.

EXAMPLES

Soluble TRANCE

The mouse TRANCE gene contains 5 exons, the first one coding essentially for the intracellular and transmembrane domain of the protein, while most of the extracellular domain is coded by the remaining 4 exons. In particular, the segment specifically coding for the in vivo functional protein domain (soluble TRANCE or sTRANCE) is coded entirely by the $3^{rd}$, $4^{th}$, and $5^{th}$ exon (Lum L. et al., J Biol Chem. (1999), 274(19): 13613-8; Kodaira K. et al., Gene (1999), 230(1), 121-127). The structure of the corresponding human gene is not known yet but a human genomic segment associated to human chromosome 13 (GenBank record NT_009935) contains the coding sequence of human TRANCE protein divided into segments which are highly similar to the exons of mouse TRANCE gene in terms of sequence and length. The length of the intronic sequences seems also similar in the two genes (FIG. 2). Recently, sTRANCE forms having slightly different N-terminal sequences have been characterized (Schlondorff J et al., J Biol Chem. (2001), 276(18):14665-74), suggesting that a functional protein domain can be reduced to the coding sequence of exons 4-5. It is also interesting to note the low homology between mouse and human TRANCE in the area surrounding the possible N-terminal sequence of sTRANCE.

If the production of a functional protein domain corresponding to soluble TRANCE is desired, a mouse or human host cell can be modified, for example, by using two contiguous or non-contiguous segments of intron 2 (20 Kb long) as targeting sequences for the homologous recombination, expressing exons 3-5. The regulatory unit will contain a transcription module, containing promoter and enhancer sequences active in human cells, and a translation module which contain a synthetic exon, with convenient 5'UTR, a Met codon and 5' splicing donor site.

Alternatively, in view of the homology between human and mouse TRANCE cDNA and protein sequence and of the recently identified forms of sTRANCE the sequence corresponding to intron 3 can be also targeted in mouse or human cells, expressing only exons 4 and 5. The construct can have a regulatory unit similar to the one used for expressing exons 3-5, but a simplified construct, including only an appropriate transcription module and a 5' untranslated region as transcription module, without a splicing module, can be also used since there is a conserved Methionine right at the beginning of exon 4 in both human and mouse TRANCE genomic sequence.

The method of the invention is useful to produce the extracellular domain of other proteins belonging to the TNF family like CD40L, CD70, FasL, which have similar gene structure (Kodaira K. et al., Gene (1999), 230(1), 121-127; Locksley R M et al., Cell. (2001),104(4):487-501).

Antiangiogenic Factors Derived From Collagen XVIII 1.alpha (Endostatin)

a) The Targeting Strategy

Endostatin belongs to a growing number of angiogenesis-related functional protein domains that are generated in vivo as proteolytic fragments of a secreted primary translational product not having any angiogenesis-related activity. As recently reviewed (Cao Y, Int. J. Biochem. Cell. Biol. (2001), 33(4): 357-69), known angiogenesis inhibitors like PEX, endostatin, or restin are the C-terminal fragments of, respectively, MMP-2, collagen XVIII 1alpha, and collagen XV, while Fn-f and vasostatin are the N-terminal fragments of, respectively, fibronectin and calreticulin.

In particular, many proteins belonging to the collagen protein family and acting as structural element of the extracellular matrix are proteolytically modified to obtain angiostatic factors, the most studied of which is known as endostatin. This functional protein domain is encoded by the collagen XVIII 1alpha (COL18A1) gene and, as a highly similar fragment called restin encoded by the collagen XV (COL15) gene, represent the C-terminal end of the non-collagenous domain (NC1) of the primary translational product (John H et al., Biochemistry (1999), 38(32): 10217-24; Sasaki T et al., J Mol Biol. (2000), 301(5): 1179-90).

The human COL18A1 gene contains 41 exons, while mouse COL18A1 gene contains 43 exons, but the NC1 domain is encoded by the last six exons in both organisms. A further distinction can be made amongst the exons of human COL18A1 gene encoding the NC1 domain amongst the ones associated to the multimerization domain (exons 36-37), a hinge region (exon 38), and an endostatin core domain (exons 39-41).

Endostatin was initially characterized in mouse as a fragment containing 183 amino acids corresponding to the last 9 amino acids encoded by exon 40 plus the amino acids encoded by exon 41-43 (O'Reilly MS et al., Cell (1997) 88(2): 277-285). However, a corresponding fragment containing the last 9 amino acids encoded by exon 38 plus the amino acids encoded by exons 39-41 has not been found in human samples. Several studies have shown that the hinge region is particular sensitive to various proteases (Felbor U et al., EMBO J. (2000), 19(6): 1187-94; Ferreras M et al., FEBS Lett.(2000), 486(3):247-51; John H et al., Biochemistry (1999), 38(32):10217-24; Wen W et al., Cancer Res. (1999), 59 (24):6052-6056), leading to a series of fragments having a different N-terminal sequence encoded by exon 38 (FIG. 3). Literature shows also that the first amino acids encoded by exon 39 are structured (Hohenester E et al., EMBO J. (1998), 17(6): 1656-64) and proteins having an N-terminal at least 4 amino acids longer or shorter compared to N-terminus of the protein encoded by exon 39-41 appear to be respectively active and inactive (Yamaguchi N et al., EMBO J. (1999), 18 (16): 4414-4423; Standker L et al., FEBS Lett. (1997), 420 (2-3):129-133). Finally, isolated or chimaeric fragments derived from different sequences encoded by exons 39-41 have variable properties regarding cell migration and proliferation (WO 00/63249, WO 00/67771).

It can be concluded that the human COL18A1 exons 39-41 encode for an autonomous folding unit of human collagen XVIII 1alpha protein corresponding to the bona fide core functional protein domain providing the angiostatic properties of natural endostatin. Moreover, literature shows also that sequences belonging to exons 36-38 or even heterologous sequences eventually added at the N-terminus of such functional protein domain, if having a limited length (Yamaguchi N et al., EMBO J. (1999), 18 (16): 4414-4423; Blezinger P et al., Nat. Biotechnol. (1999), 17 (4): 343-348), are expected not to interfere with the angiostatic properties associated to such endostatin-like functional protein domains.

The genomic DNA sequence of human COL18A1 gene, which is localized on chromosome 21 (Hattori M et al., Nature (2000), 405(6784): 311-9), is included in a 340 Kilobases genomic clone accessible through Genbank (accession number AL163302), and primers allowing the specific amplification of segments included in this clone can be easily designed. Therefore, functional protein domains having the angiostatic properties of human endostatin can be produced by modifying human cells, accordingly to the invention, using a vector containing a regulatory unit and targeting sequences which allow the integration of the regulatory unit at the level of either intron 37 or intron 38 of the human COL18A1 gene by homologous recombination.

Two different constructs (pEnd-HR#1 and pEnd-HR#2) were assembled using the same regulatory unit and different targeting sequence belonging to the human COL18A1 gene (FIG. 4A). The construct pEnd-HR#1 allows the replacement, by homologous recombination, of 3' end of intron 36, complete exon 37, and 5' end of intron 37 with a regulatory unit promoting the expression of the exons 3841. The construct pEnd-HR#2 allows the replacement, by homologous recombination, of 3' end of intron 37 and full exon 38 with a regulatory unit promoting the expression of the exons 39-41.

Cloning of the DNA segments, plasmid construction and transfection, as well as cell selection and analysis were performed using standard techniques described in the literature (Ausubel F M et al., "Current Protocols in Molecular Biology" pub. John Wiley & Sons Inc., 1999; Sambrook et al., "Molecular Cloning: A Laboratory Manual", Cold Spring Harbor Press, 1989; Hasty P et al., in "Gene targeting: a practical approach", ed. Joyner A L, pub. Oxford Univ. Press (1999), 1-35). All the plasmids were maintained and propagated prior to transfection into human cells using common *E. coli* strain DH5alpha or XL1 blue.

b) Construction of the Targeting Vectors

The cloning of COL18A1 genomic fragments necessary for generating the targeting vector was performed by amplifying, using PCR, the appropriate homology regions from the GenBank clone AL163302, in particular inside the 9.7 Kilobases segment comprised between exon 32 and 3' untranslated region of exon 41 (FIG. 4A).

The 37 base long primer o-1124 contains, at the 5' end, a 10 base long sequence including a Sal I restriction site, while the 27 bases at the 3' end correspond to the nucleotides 202790-202816 of clone AL163302. This latter sequence allows the hybridization of o-1124 within exon 32 of human COL18A1 gene, and it was used as forward primer for amplifying the 5' targeting region of both constructs.

The 36 base long primer o-1125 contains, at the 5' end, a 9 base long sequence including a Bam HI restriction site, while the 27 bases at the 3' end are complementary to the nucleotides 206301-206327 of clone AL163302. This latter sequence allows the hybridization of o-1125 within intron 36 of human COL18A1 gene, and it was used as reverse primer for amplifying the 5' targeting region of construct pEnd-HR#1.

The 35 base long primer o-1121 contains, at the 5' end, a 9 base long sequence including a Bam HI restriction site, while the 26 bases at the 3' end are complementary to the nucleotides 208099-208125 of clone AL163302. This latter sequence allows the hybridization of o-1121 within intron 37 of human COL18A1 gene, and it was used as reverse primer for amplifying the 5' targeting region of construct pEnd-HR#2.

The 35 base long primer o-1116 contains, at the 5' end, a 10 base long sequence including a XbaI restriction site, while the 25 bases at the 3' end correspond to the nucleotides 206382-206406 of clone AL163302. This latter sequence allows the hybridization of o-1116 within intron 37 of human COL18A1 gene, and it was used as forward primer for amplifying the 3' targeting region of constructs pEnd-HR#1.

The 40 base long primer o-1117 contains, at the 5' end, a 16 base long sequence including a Not I restriction site, while the 24 bases at the 3' end are complementary to the nucleotides 208098-208121 of clone AL163302.

This latter sequence allows the hybridization of o-1117 within intron 37 of human COL18A1 gene, and it was used as reverse primer for amplifying the 3' targeting region of construct pEnd-HR#1.

The 34 base long primer o-1126 contains, at the 5' end, a 9 base long sequence including a XbaI restriction site, while the 25 bases at the 3' end correspond to the nucleotides 208381-208405 of clone AL163302. This latter sequence allows the hybridization of o-1126 within intron 38 of human COL18A1 gene, and it was used as forward primer for amplifying the 3' targeting region of construct pEnd-HR#2.

The 43 base long primer o-1123 contains, at the 5' end, a 17 base long sequence including a NotI restriction site, while the 26 bases at the 3' end are complementary to the nucleotides 209828-209853 of clone AL163302. This latter sequence allows the hybridization of o-1123 within intron 39 of human COL18A1 gene, and it was used as reverse primer for amplifying the 3' targeting region of construct pEnd-HR#2.

Using the genomic clone AL163302 as template and o-1124 and o-1125 as primers, PCR leads to the generation of the 5' targeting DNA fragment of construct pEnd-HR#1. This 3.5 Kb fragment includes the 3' end of exon 32, the complete introns 32-35 and exons 33-36, the 5' end of intron 36, and the unique Sal I and Bam HI restriction sites, respectively, at the 5' and 3' ends.

Using the genomic clone AL163302 as template and o-1124 and o-1121 as primers, PCR leads to the generation of the 5' targeting fragment of construct pEnd-HR#2. This fragment of 5354 base pairs includes the 3' end of exon 32, the complete introns 32-36 and exons 33-37, the 5' end of intron 37, with the unique Sal I and BamHI restriction sites, respectively, at the 5' and 3' ends.

Using the genomic clone AL163302 as template and o-1116 and o-1117 as primers, PCR leads to the generation of the 3' targeting DNA fragment of construct pEnd-HR#1. This 1.7 Kb fragments includes a central region of intron 37, and the unique XbaI and NotI restriction sites, respectively at the 5' and 3' ends.

Using the genomic clone AL163302 as template and o-1126 and o-1123 as primers, PCR leads to the generation of the 3' targeting fragment of construct pEnd-HR#2. This 1.5 Kb fragment includes complete intron 38 and exon 39, and the 5' end of intron 39, with the XbaI and NotI unique restriction sites, respectively at the 5' and 3' ends.

Since the PCR products are particularly long, specific enzymes and procedures known in the art are preferred to amplify the fragment necessary for generating the targeting vectors. Kits for high fidelity, long range PCR are commercially available, like the Herculase PCR kit (Stratagene).

Each amplified 5' and 3' homology region was cloned, respectively, between the BamHI and Sal I sites, and XbaI and NotI sites of a plasmid pBluescript-KSII (pBS-KSII; Stratagene). The amplified and cloned genomic fragments were then analyzed by restriction mapping and partial DNA sequencing to confirm their identity.

The construction of the regulatory unit was performed by assembling DNA sequences known in the literature (FIG. 4B). The transcription module was chosen amongst the human or non-human promoters constitutively active in human cultured cells at high levels. An example is the promoter of the human elongation factor-1 (EF-1) alpha gene which has been cloned (Uetsuki T, et al., J Biol Chem. (1989), 264(10):5791-8) demonstrated to be very effective in a wide host cell range (Mizushima S and Nagata S, Nucleic Acids Res. (1990), 18(17):5322). This 1.2 Kb long promoter, present in several commercially available plasmids (InVitrogen), contains a TATA box followed by a transcription start site, which starts the transcription of a 22 base long, non translated exon and of a 0.9 Kb intron having an enhancing effect of the transcription since it contains several Sp1 and Ap1 sequences.

The translation module containing a translational initiation site was combined with a splicing module with a consensus sequence for a splice donor site. Additionally, in order to facilitate the isolation of the functional protein domain located at the 3' end of a gene, a sequence encoding for a signal peptide in-frame with the exons coding for the functional protein domain was included between the translational initiation site and the splicing consensus sequence. As signal peptide it was chosen the mouse Ig Signal Peptide (mIgSP) sequence (GenBank accession number M13329), while the splicing appropriate consensus was chosen amongst the ones recently shown as functional in human cells (Long M et al., Proc Natl Acad Sci U S A (1998), 95 (1): 219-223; Blencowe B J, Trends Biochem. Sci. (2000), 25(3): 106-110).

A fragment of human EF-1 alpha promoter (corresponding to nucleotides 373-1561 in the GenBank record J04617) was cloned between the ClaI and NheI of pBS-KSII generating the vector pBS-EF1 alpha. The exon coding for mIgSP and the splice donor site were combined in a synthetic 0.2 Kb DNA segment which contains, at the 5' end, a XbaI restriction site and, at the 3' end, NheI and NotI restriction sites. This fragment was cloned into pBS-EFlalpha between XbaI and NotI sites, such as it is located 3' to the human EF 1 alpha promoter, generating the plasmid pBS-EFlalpha-mIgSP-SD (FIG. 5).

The homologous recombination vector backbone was constructed starting from the plasmid pGEM-3Z (Promega), to which the positive and negative selection markers, the targeting regions, and the transcriptional, translational, and splicing modules were added as follows.

The gene for the negative selection for homologous recombination was the HSV-1 Thymidine Kinase (HSV-TK; a 1.8 Kb long fragment derived from the human herpesvirus 1 complete genome, deposited in GenBank as NC_001806), under the control of the ubiquitously active mouse phosphoglycerate kinase (mPGK) promoter and polyadenylation signal (respectively, 508- and a 480-base long fragments derived from the plasmid deposited in GenBank as X76683).

The multiple cloning site in 3' to HSV-TK was modified to allow the cloning of all the other elements. Two new unique restriction sites NotI and ClaI were introduced by cloning two annealed oligonucleotides, while two XbaI sites nearby the mPGK promoter and polyadenylation site were eliminated by sequential digestion and religation, generating the plasmid pGEM-3Z-mPGK-TK-HR (FIG. 6). This latter plasmid was used to clone, for each construct, first the 5' targeting region, then the positive selection marker, and finally the 3' targeting region together with the transcription/translation module.

The 5' targeting region of each construct was cut from the pBS-KSII vector using the Bam HI and Sal I restriction sites, and then subcloned into pGEM-3Z-PGK-TK-HR between the Bam HI and Xho I sites, resulting into plasmids pGEM-3Z-PGK-TK-5'HR#1 and pGEM-3Z-mPGK-TK-5'HR#2. The hygromycin resistance gene was chosen as the positive selection gene and was obtained from the plasmid pHygEGFP (Clontech), in which the resistance gene is expressed under the control of a viral promoter (CMV) as a fusion protein with the Green Fluorescent Protein (GFP). The commercial plasmid was modified to remove the two adjacent NotI sites by cutting with NotI and filling in with Klenow enzyme (Life Technologies). The CMV-HygEGFP-polyA cassette was then cloned as a Cla I-Bgl II fragment into plasmids pGEM-3Z-PGK-TK-5'HR#1 and pGEM-3Z-mPGK-TK-5'HR#2 using the ClaI and BamHI restriction sites, generating the plasmids pGEM-3Z-PGK-TK-HYG5'HR#1 and pGEM-3Z-mPGK-TK-HYG-5'HR#2.

The 3' targeting region of each construct was cut from the pBS-KSII vector as a XbaI-NotI fragment and cloned into plasmid pBS-EF1alpha-mIgSP-SD, using the NheI and NotI sites downstream to the exon coding for the mIgSP signal peptide followed by the consensus splice donor site. The resulting plasmids pBS-EF1alpha-mIgSP-SD-3'HR#1 and pBS-EF1alpha-mIgSP-SD-3'HR#2 contain the EF1-mIgSP segment fused to the 3' targeting region between the ClaI and NotI sites. Such ClaI-NotI fragment was finally introduced between the ClaI and NotI sites of pGEM-3Z-PGK-TK-HYG-5'HR#1 and pGEM-3ZPGK-TK-HYG-5'HR#2, downstream to the positive selection cassette, obtaining the final pEnd-HR#1 (FIG. 7) and pEnd-HR#2 vector. These plasmids can be linearized at the unique NotI site located at the 3' end of the 3' targeting region before being transfected into cells for targeting the exogenous sequences into the specific locations into human COL18A1 gene. Once integrated, the regulatory unit is expected to drive the transcription of an mRNA coding for mIgSP fused in-frame either to COL18A1 exons 38-41 for pEnHR#1 (SEQ ID NO:5; SEQ ID NO:6; FIG. 8) or COL18A1 exons 39-41 for pEnd-HR#2 (SEQ ID NO:7; SEQ ID NO:8; FIG. 9).

The activity of the exogenous regulatory unit included in pEnd-HR#1 and pEnd-HR#2 were preliminarily tested by transiently transfecting pEAK plasmids containing endostatin coding sequence (Edge BioSystems). The regulatory regions were cloned in 5' to a DNA fragment containing the intronic sequence which would be transcribed and spliced following homologous recombination in human COL18A1 gene, the coding sequences in the downstream exons of human COL18A1 gene fused in-frame with an heterologous epitope helping the identification of the protein even in small quantities, a stop codon, and a polyadenylation site present in the vector (FIG. 10A). The two constructs (pEAK-pEnd-HR#1 and pEAK-pEnd-HR#2) were transfected in human 293 EBNA cells (later used for homologous recombination), which do not express COL18A1 gene (Yamaguchi N et al., EMBO J. (1999), 18 (16): 4414-4423).

The mRNA, as well as the secreted and intracellular proteins, of the transfected cells was tested to verify the correct transcription, splicing, and translation of the construct.

The analysis was first performed by RT-PCR, amplifying the cDNA obtained from the transfected cells, and then by Western blot, using antibodies commercially available for endostatin (Chemicon Inc.) and for the FLAG epitope (Amersham-Pharmacia). In particular, the protein analysis shows that the EF-1 alpha promoter is active into 293-EBNA and, following transcription and splicing, the final mRNA is translated into a functional protein domain of the expected size (FIG. 10B). This protein is then secreted in the culture medium by virtue of the exogenous signal peptide (FIG. 10C), as shown in literature with a construct containing only COL18A1 exonic sequences (Blezinger P et al., Nat. Biotechnol. (1999), 17 (4): 343-348).

c) Transfection of the Targeting Vectors and Clone Selection

The pEnd-HR#1 and pEnd-HR#2 vectors can be used to transfect human cell types in which the exogenous regulatory sequences are active, or inducible, independent of whether the endogenous COL18A1 gene is already expressed. This gene is highly expressed in the liver, heart and kidney vascular tissues, as well as in hepatocytes (Saarela J et al., Am. J. Pathol. (1998), 153 (2):611-626). Therefore, cell lines derived from these cell types can be used for applying the methods of the invention, but other cell types not expressing COL18A1 also can be used since, even if the chromatin structure at this locus may eventually repress transcription, sufficiently strong and ubiquitous active or inducible regulatory sequences can overcome such limitations. Consequently, the choice of the cell type can be expanded to immortalized human cell lines which can be easily transfected and expanded, like HT1080, WI38, HepG2, or 293 cells.

As shown before, human embryonic kidney derived cells 293-EBNA are taken as an example of a human immortalized cell line which can be effectively modified with the method of the invention to obtain the selective expression of the exons in human COL18A1 gene coding for an antiangiogenic functional protein domain. These cells, which are commercially available (InVitrogen), express Epstein-Barr virus nuclear antigen 1 (EBNA-1), can be efficiently transfected using electroporation and grow in standard Dulbecco's Modified Eagle's Medium (DMEM) containing 10% Fetal Calf Serum, 4.5 grams/liter of glucose, and antibiotics (100 micrograms/milliliter of penicillin and streptomycin; Gibco-BRL).

Transfection by electroporation was carried out using a Multiporator apparatus (Eppendorf), equipped with 4 millimeter gap electrodes, at the recommended conditions (60 microSiemens and 500 Volts) and using the hypo-osmolar buffer optimized for mammalian cells provided by the manufacturer. Eight aliquots of log phase growing 293-EBNA cells (each $2.5 \times 10^6$ cells) were electroporated with 12 micrograms of NotI linearized plasmid, either pEnd-HR#1 or pEnd-HR#2, in 800 microliters of buffer. After the pulse, a total of $2 \times 10^7$ cells transfected with the same linearized vector were plated into four tissue culture plates having a diameter of 150 millimeters (NUNC) previously coated with D-polylysine (SIGMA). After 72 hours, the selection was initiated using 250 micrograms/milliliter of hygromycin (Life Technology), with medium change every two days. After four more days under selection, the negative selection for homologous recombination was applied by incubating the cells with a tissue culture medium containing 10 micromolar Gancyclovir (Cymevene; Roche) in addition to hygromycin.

Approximately 25 days after transfection, the selected cells were isolated using pipette tips under microscope as single clones. A pool of clones was generated for each plate (approximately 300 clones/pool) and the four pools were kept under positive selection up to 4-5 weeks to be expanded and obtain sufficient material for further analysis before proceeding to select smaller pools of clones.

d) Identification and Analysis of the Clones Expressing Endostatin

Many approaches can be applied to the clones resulting after the positive-negative selection in order to identify cells in which an antiangiogenic functional protein domain is expressed as a result of the integration, by homologous recombination, of the exogenous regulatory unit in human COL18A1 gene. The following experiments were performed to confirm the correct integration of the regulatory unit and the specific expression of the exons encoding the antiangiogenic functional protein domain.

The analysis of the human COL18A1 gene and transcripts structure in the selected clones was performed on the genomic DNA and the mRNA extracted from positive pools of cells using technologies described in the literature known to the skilled in the art. The selective amplification of DNA segments using DNA primers (PCR) was preferred as a first approach since it is faster and requires less biological material, in order to identify sequences which would be comprised in the genomic DNA and in the mRNA after correct targeting and splicing (FIG. 11A-B). Some of the amplified segment were also cloned and submitted to DNA sequencing for a further confirmation of sequence identity.

PCR was performed on an Applied Biosystem 9700 thermocycler using either the HotStarTAQ PCR (when the initial material is genomic DNA or cDNA) or OneStep HotStar RT-PCR (when the initial material is total RNA) commercial kits (Qiagen), essentially as described by the manufacturer. The final volume of the reactions was either 25 or 50 microliters. Following the completion of the PCR reaction, 10 or 20 microliters of the reaction mix were then run on agarose gels and screened for the presence of the expected PCR fragments which would indicate either the proper integration of the exogenous sequence in the targeted position of COL18A1 gene, or the presence of the expected spliced mRNA coding for the antiangiogenic functional protein domain.

Pools of clones transfected with pEnd-HR#1 or pEnd-HR#2 were first screened for the presence of the new transcripts. The mRNA extracted from the clones was either reverse transcribed and then amplified by PCR (two-steps approach), or directly reverse transcribed and amplified in same tube (one-step approach), or directly reverse transcribed and amplified in same tube (one-step approach). The primers were designed to hybridize with the template in different exonic sequences, keeping the same forward primer hybridizing in the mIgSP exon, and using different reverse prier hybridizing wit human endogenous COL18A1 exon (FIG. 11A).

For the two-steps approach, one microgram of total RNA was reverse-transcribed with oligo-$dT_{18}$ primers using the Superscript-II cDNA kit (Life-technologies), as described by the manufacturer, and 5 units of MMLV Reverse Transcriptase (Promega Biotech). After an incubation for 45 minutes at 37° C., RNase H was added (1 unit) to eliminate the RNA paired to DNA extended from the oligonucleotides, and the incubation at 37° C. was prolonged for 15 minutes more. The resulting complementary DNA (cDNA) was finally diluted to a 10 nanograms/microliter concentration using RNase-free water. The PCR was then performed using 20 nanograms of oligo-dT primed cDNA and 0.5 microMolar of each primer, and applying the following program:

1×95° C. for 15 minutes;
5× of 95° C. for 45 seconds, 60° C. to 56° C. (decreasing 1° C. at each cycle), 72° C. for 1 minute;
35×95° C. for 45 seconds, 54° C. for 30 seconds, and 72° C. for 1 minute; 1×72° C. for 10 minutes.

For the one-step approach, the OneStep HotStar RT-PCR was performed by using 500 nanograms of total RNA and 0.5 microMolar of each primer. The reverse transcription reaction was performed at 50° C. for 30 minutes according to the conditions given by manifacturer, and then the following program was applied:

1×95° C. for 15 minutes;
35×95° C. for 30 seconds, 57° C. for 30 seconds, 72° C. for 1 minute;
1×72° C. for 10 minutes.

Initially the oligonucleotide hybridizing within the coding region in the exogenous mIgSP exon was used together with a primer hybridizing in the endogenous COL18A1 exon 40, which should be expressed following the integration of any of the two constructs in human COL18A1 gene. Amplifying cDNA generated using mRNA extracted from pools of selected clones which were transfected with either pEnd-HR#1 or pEnd-HR#2, it was possible to identify a pool of clones for each targeting construct (pool 4 containing for pEnd-HR#1 and pool 3 for pEnd-HR#2) which expresses an mRNA molecule having both the exogenous and endogenous exonic sequences separated by the number of nucleotides expected after correct targeting, transcription, and splicing (577 bases for pEnd-HR#1, 331 bases for pEnd-HR#2). The PCR was negative for the untransfected cells (FIG. 12).

In the pool of pEnd-HR#1 positive clones it was possible to identify a minor band apparently corresponding to the size expected for pEnd-HR#2. Hence, a detailed PCR analysis was made on each of the two molecular species using the more external primer o-1165 and o-1131 and the pool 4 of pEnd-HR#1 positive clones, two larger bands (FragA and FragB) were amplified, having the same difference in length observed using the more internal reverse primer o-1175. Such fragments were isolated from gel, cloned, and used separately as template with o-1165 as forward primer and other oligonucleotides as reverse nested primers: o-1164, o-1175, o-1179.

If the minor band would result from an alternative splicing, the amplified fragments obtained using FragA and FragB as template should differe by a segment corresponding to the length of the lacking exon. Since all the couples of primers amplify fragments which differ by approximately 250 base pairs between FragA and FragB, it can be concluded that the minor band originally identified in pool 4 corresponded actually to a transcript in which exon 38 (246 bases), comprised in all the fragments, was spliced out due to an alternative splicing event (FIG. 13). This irregular splicing, which was later confirmed by sequencing the cloned fragments, leads however to a transcript identical to the one obtained transfecting the cells with pEnd-HR#2, since exon 38 and 39 have the same frame (FIG. 8).

Finally, a 0.9 Kb fragment was obtained by RT-PCR on mRNA from pool 4 of pEnd-HR#1 transfected cells using the mIgSP specific primer o-1165 and the primer o-1193 which is specific for the 5' untranslated region of exon 41. This fragment was cloned and sequenced. The sequence corresponded to the expected one (FIG. 8), further confirming that the DNA construct was integrated correctly for driving the transcription of the targeted COL18A1 exons specific for endostatin.

Further analysis on the pool of clones transfected with pEnd-HR#1 and expressing the correct transcript was made at the genomic level using PCR with oligonucleotides hybridizing with either exonic, as in the case of o-1165 and o-1166, or intronic, as in the case of o-1168 and o-1121 sequences (FIG. 11B).

PCR was performed using 200 nanograms of genomic DNA (isolated from pEnd-HR#1 positive pools of clones identified by RT-PCR, or from 293-EBNA untransformed cells) and 0.5 micromolar of each primer, applying the following program:
1×95° C. for 15 minutes;
5×95° C. for 30 seconds, 62° C.–58° C. for 30 seconds (decreasing 1° C. at each cycle), 72° C. for 2 minutes 15 seconds;
25×95° C. for 30 seconds, 57° C. for 30 seconds, 72° C. for 2 minutes 15 seconds;
1×72° C. for 10 minutes.

The primers hybridizing in the exonic regions (one inserted by homologous recombination, the other endogenous) were able to amplify a fragment of expected length (1820 bases) in all the pools of clones generated from the original positive pool but not in untransfected cells (FIG. 14A), confirming the integration of the mIgSP exon. The primers hybridizing in the intronic regions were able to amplify a fragment of expected length (1784 based) in both transfected and untransfected clones, confirming the integrity of the gene structure (FIG. 14B).

Further evidence that the gene structure is the one expected after the integration of the regulatory unit contained in targeting vector pEnd-HR#1 was obtained by digesting the fragments obtained using the exon- and intron-specific primers with a series of restriction enzymes to verify that the resulting subfragments were of the expected length. All the tested enzymes provided the expected restriction pattern (FIG. 15A, B).

The PCR analysis, performed on the mRNA and genomic DNA extracted from cells modified by the methods of the invention, allowed the identification of clones wherein the integration of a regulatory unit in human COL18A1 gene, causes the specific expression of the exons coding for the functional protein domain determining the angiostatic properties of endostatin. Therefore, the analysis can go further in isolating and characterizing the clone best expressing the desired functional protein domain. This additional analysis can be performed at the level of by hybridizing endostatin specific probes with total RNA (Northern blot) or genomic DNA (Southern blot) obtained from these clones after being sufficiently expanded. For example, the Souther blot should allow the identification of a 2.2 Kb or 1.9 Kb band in the RNA isolated from clones transfected with, respectively, pEnd-HR#1 or pEnd-HR#2. If the genomic DNA of positive cells and untransfected cells is digested with NheI and SpeI is separated on a agarose gel, transferred on a filter and probed with a radioactive fragment corresponding to the human COL18A1 genomic region including exon 32-36 and intron 32-36, the hybridization pattern would differ since the 12.4 Kb fragment, including human COL18A1 from intron 31 to the end, visible in the untransfected cells would be replaced by a shorter fragment in positive cells (4.4 Kb in pEnd-HR#1 transfected cells) due to the additional NheI and SpeI sites in the gene for the positive selection.

At the protein level, before further expansion, collection, and purification of the angiostatic functional protein domains, the screening can proceed using antibody-based technologies (ELISA, Western Blot, immunoprecipitation), in order to identify the clones having the higher production levels.

The antiangiogenic activity of the functional protein domains further purified can be determined by one of the several methods described in the literature based on endothelial cells. Protein extracts, purified preparations or culture media obtained from the positive clones can be tested in an endothelial cell migration assay, using recombinant or purified human endostatin as a standard. One of the more common assays employs human umbilical vein endothelial cells (HUVECs), which are commercially available (Clonetics) and can be cultured to build a reliable migration test (Yamaguchi N et al., EMBO J.(1999), 18(16);4414-4423).

Trx80

Human thioredoxin (Trx) is an enzyme catalyzing intracellular disulfide reductions. A truncated form of thioredoxin (Trx80), containing the 80-84 N-terminal residues and lacking any enzymatic activity, is cleaved and secreted by monocytic cell lines and, by itself, it is a potent mitogenic cytokine stimulating growth of resting human peripheral blood mononuclear cells (Pekkari K et al., J Biol. Chem. (2000), 275(48): 37474-80). Moreover, purified human CD14(+) monocytes medium were specifically activated to differentiation by Trx80 as measured by the increased expression of CD14, CD40, CD54, CD86. Trx80 induces also the secretion of IL-12 from CD40(+) monocytes in human peripheral blood mononuclear cells cultures, an effect enhanced by IL-2 which induces secretion of interferon-gamma in PBMC cultures (Pekkari K et al., Blood. 2001 May 15;97(10):3184-90). Even though Trx may have some co-cytokine activity with interleukins after leaderless secretion (Bertini R et al., J Exp Med.(1999), 189(11):1783-9), the effects obtained with Trx80 are not reproducible using the complete protein.

Human Trx gene (GenBank records X54539 and X54540) contains five exons coding for a protein containing 105 residues, (Kaghad M et al., Gene (1994), 140(2), 273-8). The first 4 exons, all having frame zero, encodes for a total of 85 residues and correspond essentially to Trx80. The 1.3 Kb sequence containing intron 4, exons 4-5 and part of intron 3 (GenBank record X70288) can be used for constructing a targeting vector allowing the integration of a regulatory unit for terminating transcription and translation, together with a splicing acceptor site, at the level of intron 4.

Human Tyrosine-tRNA Synthetase Derived Cytokines

Aminoacyl-tRNA synthetases catalyze aminoacylation of transfer RNAs (tRNAs). While native human tyrosyl-tRNA synthetase is inactive as a cell-signaling molecule, it can be secreted and split into two distinct cytokines under apoptotic conditions, probably by the leukocyte elastase, an extracellular protease (Wakasugi K and Schimmel P, Science (1999), 284(5411): 147-51). The N-terminal fragment that harbors the catalytic site acts as an interleukin 8-like cytokine. The C-terminal domain is an endothelial-monocyte-activating polypeptide II (EMAP II)-like cytokine, having a potent leukocyte and monocyte chemotaxis activity and stimulating production of myeloperoxidase and tumor necrosis factor-alpha.

The putative cleavage site of the protein, which contains 528 residues, is located at residue 360 but fragments obtained by cleaving at residue 344 are active as well. By using the known coding sequence of tyrosyl-tRNA synthetase (GenBank record BC001933) to search human genome, a genomic clone containing interrupted sequences corresponding to human tyrosyl-tRNA synthetase coding sequence can be found (GenBank record AL356780). In particular, the sequence coding for amino acids 303-348 and 349-380 corresponds, respectively, to the sequences 98110-97970 and 96712-96615 of the human clone, which has an opposite numbering orientation.

In this situation, the segment of the clone comprised between 98110 and 96615, as well other surrounding sequences available in the clone, can be used for targeting a regulatory unit either initiating or terminating transcription and translation between 97970 and 96712, depending if the expression of the N-terminal (amino acids 1-348) or C-terminal (amino acids 349-528) cytokine is desired.

Antigen Binding Site of an Immunoglobulin Heavy Chain

In some embodiments, the regulatory unit may contain a sequence capable of terminating the transcription and translation in a position corresponding to the 5' end of the functional protein domain. Such an approach can be applied whenever the functional protein domain of interest is located in the first exon(s) of the target gene and the target gene is constitutively or, following induction, highly expressed in the cell where the method is applied.

An example is represented by the binding sites of antibodies, which are located at the N-terminus of an immunoglobulin molecule. The antigen binding sites of conventional antibodies are formed primarily by the hypervariable loops from both the heavy and the light chain variable domains. Functional antigen binding sites can however also be formed by heavy chain variable domains (VH) alone, as in camels and camelids, where antibodies contain only two heavy chains variable domains and lack light chains. Analysis of the differences in amino acid sequence between the VHs of these camel heavy chain-only antibodies and VH domains from conventional human antibodies helped to design an altered human VH domain. This camelised VH proved, like the camel VH, to be a small, robust and efficient recognition unit formed by a single immunoglobulin (Ig) domain (Riechmann L. et al., J Immunol Methods. 1999 Dec. 10;231(1-2):25-38; Davies J. et al., Biotechnology (NY), 1995 May; 13(5):475-9).

The exon coding the VH domain of an IgG results from the rearrangement and mutation occurring during B cell development. Once that a myeloma cell is fused to a B cell coding for an antibody having high affinity for an antigen, the resulting hybridoma cells transcribe and translate actively the complete IgG gene, but these cells may also integrate exogenous sequences by homologous recombination at high efficiency (Shulman M J et al., Mol Cell Biol. (1990) 10(9): 4466-4472). If one desires to obtain only the VH domain as a functional protein domain, the IgG gene can be modified using the method of the invention integrating, by homologous recombination, a regulator unit containing transcription and translation termination modules in the intron following the relevant exon.

The invention claimed is:

1. A method of producing a biologically active protein, which is a fragment of a biologically active primary translational product of an endogenous target gene, said protein being either the carboxy- or amino-terminal fragment of said primary translational product, wherein said protein is the extracellular binding domain of a membrane receptor or a proteolytic fragment of a structural extracellular matrix protein and has a biological activity which is distinct from the biological activity of said primary translational product, the method comprising:

(i) culturing a host cell in which the target gene is endogenous, which host cell has been transfected with a DNA construct comprising:

(a) a regulatory DNA segment which binds a regulatory polypeptide which can initiate or terminate transcription of the DNA encoding said protein and/or which is transcribed into a regulatory mRNA fragment capable of binding a regulatory polypeptide which can initiate or terminate translation of the mRNA encoding said protein, wherein said regulatory DNA segment allows the initiation of the transcription of the DNA encoding said protein and/or is transcribed into a regulatory mRNA fragment capable of binding a regulatory polypeptide which can initiate translation of the mRNA encoding said protein when said protein is the C-terminal fragment of said primary translational product, or wherein said regulatory DNA segment allows the termination of the transcription of the DNA encoding said protein and/or is transcribed into a regulatory mRNA fragment capable of binding a regulatory polypeptide which can terminate translation of the mRNA encoding said protein when said protein is the N-terminal fragment of said primary translational product; and (b) a DNA targeting segment comprising sequences homologous to a region of the target gene either 5' or 3' to the sequence coding for said protein, the construct being integrated within the host cell genomic DNA at a position determined by the DNA targeting segment such that expression of said protein is at least partially under control of the regulatory DNA segment;

(ii) producing said protein from the transfected host cell; and (iii) collecting said produced protein.

2. A method as claimed in claim 1, wherein the targeting region consists of two targeting segments.

3. A method as claimed in claim 1, wherein the construct further comprises one or more genes selected from the group consisting of a positive selectable marker gene and an amplifiable marker gene.

4. A method as claimed in claim 1, wherein said protein is Endostatin.

5. The method of claim 1, wherein said protein is soluble TRANCE (TNF-Related Activation Induced Cytokines).

6. The method of claim 1, wherein said protein is the extracellular binding domain of a membrane receptor.

7. The method of claim 1, wherein said protein is a proteolytic fragment of a structural extracellular matrix protein.

8. The method of claim 7, wherein said proteolytic fragment of a structural extracellular matrix protein has antiangiogenic properties.

9. A method in accordance with claim 1, wherein said protein is the C-terminal fragment of said primary translational product and said regulatory DNA segment allows the initiation of the transcription of the DNA encoding said protein and/or is transcribed into a regulatory mRNA fragment capable of binding a regulatory polypeptide which can initiate translation of the mRNA encoding said protein.

10. A method in accordance with claim 1, wherein said protein is the N-terminal fragment of said primary translational product and said regulatory DNA segment allows the termination of the transcription of the DNA encoding said protein and/or is transcribed into a regulatory mRNA fragment capable of binding a regulatory polypeptide which can terminate translation of the mRNA encoding said protein.

* * * * *

SEQUENCE LISTING

```
<160> NUMBER OF SEQ ID NOS: 8

<210> SEQ ID NO 1
<211> LENGTH: 59
<212> TYPE: PRT
<213> ORGANISM: Mus musculus

<400> SEQUENCE: 1

Lys Gln Ala Phe Gln Gly Ala Val Gln Lys Glu Leu Gln His Ile Val
1               5                   10                  15

Gly Pro Gln Arg Phe Ser Gly Ala Pro Ala Met Met Glu Gly Ser Trp
            20                  25                  30

Leu Asp Val Ala Gln Arg Gly Lys Pro Glu Ala Gln Pro Phe Ala His
        35                  40                  45

Leu Thr Ile Asn Ala Ala Ser Ile Pro Ser Gly
    50                  55
```

```
<210> SEQ ID NO 2
<211> LENGTH: 59
<212> TYPE: PRT
<213> ORGANISM: Homo sapiens

<400> SEQUENCE: 2

Lys Gln Ala Phe Gln Gly Ala Val Gln Lys Glu Leu Gln His Ile Val
1               5                   10                  15

Gly Ser Gln His Ile Arg Ala Glu Lys Ala Met Val Asp Gly Ser Trp
            20                  25                  30

Leu Asp Leu Ala Lys Arg Ser Lys Leu Glu Ala Gln Pro Phe Ala His
        35                  40                  45

Leu Thr Ile Asn Ala Thr Asp Ile Pro Ser Gly
    50                  55

<210> SEQ ID NO 3
<211> LENGTH: 312
<212> TYPE: PRT
<213> ORGANISM: Homo sapiens

<400> SEQUENCE: 3

Val Arg Leu Trp Ala Thr Arg Gln Ala Met Leu Gly Gln Val His Glu
1               5                   10                  15

Val Pro Glu Gly Trp Leu Ile Phe Val Ala Glu Gln Glu Leu Tyr
            20                  25                  30

Val Arg Val Gln Asn Gly Phe Arg Lys Val Gln Leu Glu Ala Arg Thr
        35                  40                  45

Pro Leu Pro Arg Gly Thr Asp Asn Glu Val Ala Ala Leu Gln Pro Pro
    50                  55                  60

Val Val Gln Leu His Asp Ser Asn Pro Tyr Pro Arg Arg Glu His Pro
65                  70                  75                  80

His Pro Thr Ala Arg Pro Trp Arg Ala Asp Asp Ile Leu Ala Ser Pro
                85                  90                  95

Pro Arg Leu Pro Glu Pro Gln Pro Tyr Pro Gly Ala Pro His His Ser
            100                 105                 110

Ser Tyr Val His Leu Arg Pro Ala Arg Pro Thr Ser Pro Pro Ala His
        115                 120                 125

Ser His Arg Asp Phe Gln Pro Val Leu His Leu Val Ala Leu Asn Ser
    130                 135                 140

Pro Leu Ser Gly Gly Met Arg Gly Ile Arg Gly Ala Asp Phe Gln Cys
145                 150                 155                 160

Phe Gln Gln Ala Arg Ala Val Gly Leu Ala Gly Thr Phe Arg Ala Phe
                165                 170                 175

Leu Ser Ser Arg Leu Gln Asp Leu Tyr Ser Ile Val Arg Arg Ala Asp
            180                 185                 190

Arg Ala Ala Val Pro Ile Val Asn Leu Lys Asp Glu Leu Leu Phe Pro
        195                 200                 205

Ser Trp Glu Ala Leu Phe Ser Gly Ser Glu Gly Pro Leu Lys Pro Gly
    210                 215                 220

Ala Arg Ile Phe Ser Phe Asp Gly Lys Asp Val Leu Arg His Pro Thr
225                 230                 235                 240

Trp Pro Gln Lys Ser Val Trp His Gly Ser Asp Pro Asn Gly Leu Tyr
                245                 250                 255

Arg Arg Leu Thr Glu Ser Tyr Cys Glu Thr Trp Arg Thr Glu Ala Pro
            260                 265                 270

Ser Ala Thr Gly Gln Ala Ser Ser Leu Leu Gly Gly Arg Leu Leu Gly
        275                 280                 285
```

Gln Ser Ala Ala Ser Cys His His Ala Tyr Ile Val Leu Cys Ile Glu
    290                 295                 300

Asn Ser Phe Met Thr Ala Ser Lys
305                 310

<210> SEQ ID NO 4
<211> LENGTH: 63
<212> TYPE: DNA
<213> ORGANISM: Artificial
<220> FEATURE:
<223> OTHER INFORMATION: synthetic construct

<400> SEQUENCE: 4
atgaaatgca gctgggttat cttcttcctg atggcagtgg ttacaggggt caattcggtg    60
agt                                                                 63

<210> SEQ ID NO 5
<211> LENGTH: 900
<212> TYPE: DNA
<213> ORGANISM: Artificial
<220> FEATURE:
<223> OTHER INFORMATION: synthetic construct

<400> SEQUENCE: 5
gcaccggact cagattcgct agagcgtcac ccctagagtc gagctgtgac ggtccttaca    60
atgaaatgca gctgggttat cttcttcctg atggcagtgg ttacaggggt gaattcggac   120
aatgaagtgg ccgccttgca gccccccgtg gtgcagctgc acgacagcaa ccccctaccca  180
cggcgggagc accccacccc caccgcgcgg ccctggcggg cagatgacat cctggccagc   240
cccccctcgcc tgcccgagcc ccagccctac cccggagccc cgcaccacag ctcctacgtg   300
cacctgcggc cggcgcgacc cacaagccca cccgcccaca gccaccgcga cttccagccg    360
gtgctccacc tggttgcgct caacagcccc tgtcaggcg gcatgcgggg catccgcggg     420
gccgacttcc agtgcttcca gcaggcgcgg gccgtggggc tggcgggcac cttccgcgcc    480
ttcctgtcct cgcgcctgca ggacctgtac agcatcgtgc ccgtgccga ccgcgcagcc     540
gtgcccatcg tcaacctcaa ggacgagctg ctgtttccca gctgggaggc tctgttctca    600
ggctctgagg gtccgctgaa gcccggggca cgcatcttct cctttgacgg caaggacgtc    660
ctgaggcacc ccacctggcc ccagaagagc gtgtggcatg gctcggaccc caacgggcgc    720
aggctgaccg agagctactg tgagacgtgg cggacggagg ctcccctcggc cacgggccag   780
gcctcctcgc tgctgggggg caggctcctg ggcagagtg ccgcgagctg ccatcacgcc     840
tacatcgtgc tctgcattga aacagcttc atgactgcct ccaagtagcc accgcctgga    900

<210> SEQ ID NO 6
<211> LENGTH: 275
<212> TYPE: PRT
<213> ORGANISM: Artificial
<220> FEATURE:
<223> OTHER INFORMATION: synthetic construct

<400> SEQUENCE: 6

Met Lys Cys Ser Trp Val Ile Phe Phe Leu Met Ala Val Val Thr Gly
1               5                   10                  15

Val Asn Ser Asp Asn Glu Val Ala Ala Leu Gln Pro Pro Val Val Gln
                20                  25                  30

Leu His Asp Ser Asn Pro Tyr Pro Arg Arg Glu His Pro His Pro Thr
            35                  40                  45

Ala Arg Pro Trp Arg Ala Asp Asp Ile Leu Ala Ser Pro Pro Arg Leu
        50                  55                  60

Pro Glu Pro Gln Pro Tyr Pro Gly Ala Pro His Ser Ser Tyr Val
65                  70                  75                  80

His Leu Arg Pro Ala Arg Pro Thr Ser Pro Pro Arg His Ser His Arg
                85                  90                  95

Asp Phe Gln Pro Val Leu His Leu Val Ala Leu Asn Ser Pro Leu Ser
            100                 105                 110

Gly Gly Met Arg Gly Ile Arg Gly Ala Asp Phe Gln Cys Phe Gln Gln
        115                 120                 125

Ala Arg Ala Val Gly Leu Ala Gly Thr Phe Arg Ala Phe Leu Ser Ser
    130                 135                 140

Arg Leu Gln Asp Leu Tyr Ser Ile Val Arg Arg Ala Asp Arg Ala Ala
145                 150                 155                 160

Val Pro Ile Val Asn Leu Lys Asp Glu Leu Leu Phe Pro Ser Trp Glu
                165                 170                 175

Ala Leu Phe Ser Gly Ser Glu Gly Pro Leu Lys Pro Gly Ala Arg Ile
            180                 185                 190

Phe Ser Phe Asp Gly Lys Asp Val Leu Arg His Pro Thr Trp Pro Gln
        195                 200                 205

Lys Ser Val Trp His Gly Ser Asp Pro Asn Gly Arg Arg Leu Thr Glu
    210                 215                 220

Ser Tyr Cys Glu Thr Trp Arg Thr Glu Ala Pro Ser Ala Thr Gly Gln
225                 230                 235                 240

Ala Ser Ser Leu Leu Gly Gly Arg Leu Leu Gly Gln Ser Ala Ala Ser
                245                 250                 255

Cys His His Ala Tyr Ile Val Leu Cys Ile Glu Asn Ser Phe Met Thr
            260                 265                 270

Ala Ser Lys
        275

<210> SEQ ID NO 7
<211> LENGTH: 650
<212> TYPE: DNA
<213> ORGANISM: Artificial
<220> FEATURE:
<223> OTHER INFORMATION: synthetic construct

<400> SEQUENCE: 7
gcaccggact cagattcgct agagcgtcac ccctagagtc gagctgtgac ggtccttaca      60
atgaaatgca gctgggttat cttcttcctg atggcagtgg ttacaggggt gaattcgctc     120
cacctggttg cgctcaacag ccccctgtca ggcggcatgc ggggcatccg cggggccgac     180
ttccagtgct tccagcaggc gcgggccgtg gggctggcgg caccttccg cgccttcctg      240 tcctcgcgcc tgcaggacct gtacagcatc gtgcgccgtg ccgaccgcgc agccgtgccc     300
atcgtcaacc tcaaggacga gctgctgttt cccagctggg aggctctgtt ctcaggctct     360
gagggtccgc tgaagcccgg ggcacgcatc ttctcctttg acggcaagga cgtcctgagg     420 cacccccacct ggccccagaa gagcgtgtgg catggctcgg accccaacgg cgcaggctg      480 accgagagct actgtgagac gtggcggacg gaggctccct cggccacggg ccaggcctcc     540
tcgctgctgg ggggcaggct cctggggcag agtgccgcga ctgccatca cgcctacatc      600 gtgctctgca ttgagaacag cttcatgact gcctccaagt agccaccgcc               650

<210> SEQ ID NO 8
<211> LENGTH: 193

```
<212> TYPE: PRT
<213> ORGANISM: Artificial
<220> FEATURE:
<223> OTHER INFORMATION: synthetic construct

<400> SEQUENCE: 8

Met Lys Cys Ser Trp Val Ile Phe Phe Leu Met Ala Val Val Thr Gly
1               5                   10                  15

Val Asn Ser Leu His Leu Val Ala Leu Asn Ser Pro Leu Ser Gly Gly
                20                  25                  30

Met Arg Gly Ile Arg Gly Ala Asp Phe Gln Cys Phe Gln Gln Ala Arg
            35                  40                  45

Ala Val Gly Leu Ala Gly Thr Phe Arg Ala Phe Leu Ser Ser Arg Leu
        50                  55                  60

Gln Asp Leu Tyr Ser Ile Val Arg Arg Ala Asp Arg Ala Ala Val Pro
65                  70                  75                  80

Ile Val Asn Leu Lys Asp Glu Leu Leu Phe Pro Ser Trp Glu Ala Leu
                85                  90                  95

Phe Ser Gly Ser Glu Gly Pro Leu Lys Pro Gly Ala Arg Ile Phe Ser
                100                 105                 110

Phe Asp Gly Lys Asp Val Leu Arg His Pro Thr Trp Pro Gln Lys Ser
            115                 120                 125

Val Trp His Gly Ser Asp Pro Asn Gly Arg Arg Leu Thr Glu Ser Tyr
    130                 135                 140

Cys Glu Thr Trp Arg Thr Glu Ala Pro Ser Ala Thr Gly Gln Ala Ser
145                 150                 155                 160

Ser Leu Leu Gly Gly Arg Leu Leu Gly Gln Ser Ala Ala Ser Cys His
                165                 170                 175

His Ala Tyr Ile Val Leu Cys Ile Glu Asn Ser Phe Met Thr Ala Ser
            180                 185                 190

Lys
```